US010172353B2

(12) United States Patent
Tronsmo et al.

(10) Patent No.: US 10,172,353 B2
(45) Date of Patent: Jan. 8, 2019

(54) COMPOSITION COMPRISING CHITOSAN AND A FUNGICIDE

(71) Applicant: BioCHOS AS, Ski (NO)

(72) Inventors: Arne Tronsmo, Aas (NO); Berit Bjugan Aam, Ski (NO); Linda Hjeljord, Aas (NO); Morten Sorlie, Aas (NO); Md Hafizur Rahman, Aas (NO); Anne Line Norberg, Oppegard (NO); Vincent Eijsink, Aas (NO)

(73) Assignee: BIOCHOS AS, Ski (NO)

( * ) Notice: Subject to any disclaimer, the term of this patent is extended or adjusted under 35 U.S.C. 154(b) by 0 days.

(21) Appl. No.: 14/437,530

(22) PCT Filed: Oct. 22, 2013

(86) PCT No.: PCT/EP2013/072099
§ 371 (c)(1),
(2) Date: Apr. 22, 2015

(87) PCT Pub. No.: WO2014/064119
PCT Pub. Date: May 1, 2014

(65) Prior Publication Data
US 2015/0296777 A1    Oct. 22, 2015

(30) Foreign Application Priority Data
Oct. 22, 2012 (GB) .................................. 1218954.4

(51) Int. Cl.
| A01N 31/16 | (2006.01) |
| A01N 43/16 | (2006.01) |
| A01N 63/02 | (2006.01) |
| C05F 1/00 | (2006.01) |
| C05F 11/00 | (2006.01) |
| C05G 3/02 | (2006.01) |
| A01N 43/36 | (2006.01) |
| A01N 43/40 | (2006.01) |
| A01N 43/54 | (2006.01) |
| A01N 43/56 | (2006.01) |

(52) U.S. Cl.
CPC ............. *A01N 43/16* (2013.01); *A01N 43/36* (2013.01); *A01N 43/40* (2013.01); *A01N 43/54* (2013.01); *A01N 43/56* (2013.01); *A01N 63/02* (2013.01); *C05F 1/005* (2013.01); *C05F 11/00* (2013.01); *C05G 3/02* (2013.01); *Y02A 40/203* (2018.01); *Y02P 20/145* (2015.11)

(58) Field of Classification Search
CPC ........ A01N 43/16; A01N 43/56; A01N 43/54; A01N 43/40; A01N 43/32; A01N 63/02; Y02P 20/145; C05F 11/00; C05F 1/005; C05G 3/02
USPC ......................................................... 514/55
See application file for complete search history.

(56) References Cited

U.S. PATENT DOCUMENTS

| 5,374,627 A | 12/1994 | Ito et al. |
| 5,811,095 A | 9/1998 | Williamson et al. |
| 5,965,545 A | 10/1999 | Ben-Shalom et al. |
| 2007/0161512 A1 | 7/2007 | Smith et al. |
| 2008/0220974 A1 | 9/2008 | Lopretti |

FOREIGN PATENT DOCUMENTS

| CN | 101385470 | | 3/2009 | |
| CN | 101816305 | | 9/2010 | |
| CN | 102302037 | | 1/2012 | |
| CN | 102302037 B | * | 1/2012 | ............. A01N 57/74 |
| CN | 102302037 B | * | 1/2012 | ............. A01N 57/74 |
| CN | 102939977 | | 2/2013 | |
| DE | 196 33 502 | | 2/1998 | |
| EP | 0368253 | * | 5/1990 | ............. A61K 47/36 |
| ES | 2 442 973 | | 2/2014 | |
| JP | 62-198604 | | 9/1987 | |
| WO | 00/32041 | | 6/2000 | |
| WO | WO 00/32041 | * | 6/2000 | |
| WO | 00/59949 | | 10/2000 | |
| WO | 01/52655 | | 7/2001 | |
| WO | 2008/065151 | | 6/2008 | |
| WO | 2010/015913 | | 2/2010 | |
| WO | WO 2010/015913 A2 | * | 2/2010 | ............. A01N 43/16 |
| WO | 2010/029067 | | 3/2010 | |
| WO | 2010/125065 | | 11/2010 | |
| WO | 2012/101106 | | 8/2012 | |
| WO | 2013/178856 | | 12/2013 | |

OTHER PUBLICATIONS

Yoonkung et al, J. Microbiol. Biotechnol, 2008, 18(10), 1729-1734.*
Rahman, Ph.D. Thesis, Univ. of Norway, 2012, Paper IV, pp. 1-25.*
Ghaouth, A.E. et al., Antifungal Activity of Chitosan on Post-Harvest Pathogens: Induction of Morphological and Cytological Alterations an Rhizopus Stolonifer, Mycological Research, 1992, vol. 96, No. 9, pp. 769-779.
Park, Y. et al., Investigation of the Antifungal Activity and Mechanism of Action of LMWS-Chitosan, J. Microbiol. Biotechnol. (2008) 18(10), 1729-1734.
International Search Report for PCT/EP2013/072099, dated Dec. 6, 2013.
Badawy et al., "A Biopolymer Chitosan and Its Derivatives as Promising Antimicrobial Agents against Plant Pathogens and Their Applications in Crop Protection", International Journal of Carbohydrate Chemistry, 2011:21-29 (2011)

(Continued)

*Primary Examiner* — Ganapathy Krishnan
(74) *Attorney, Agent, or Firm* — Wenderoth, Lind & Ponack, L.L.P.

(57) ABSTRACT

The present invention provides a composition comprising (i) chitosan or chitopoly- or chitooligo-saccharides thereof, wherein said chitosan or chitopoly- or chitooligo-saccharides thereof comprise β-(1-4)-linked D-glucosamine and N-acetyl-D-glucosamine monomers and have a degree of acetylation between 0.05 and 0.20 and an average degree of polymerization ≤250 (molecular weight ≤42,000 Da), and (ii) a fungicide not containing chitopoly- or chitooligo-saccharides.

24 Claims, 4 Drawing Sheets

(56) References Cited

OTHER PUBLICATIONS

Gisi, "Synergistic Interaction of Fungicides in Mixtures", Phytopathology, 86(11):1273-1279 (1996).
Jaime et al., "Identification of yeast genes that confer resistance to chitosan oligosaccharide (COS) using chemogenomics", BMC Genomics, 13(267):1-26 (2012).
Kendra et al., "Characterization of the Smallest Chitosan Oligomer That is Maximally Antifungal to *Fusarium solani* and Elicits Pisatin Formation in *Pisum salivum*", Experimental Mycology, 8:276-281 (1984).
Rahman, "Antifungal activity of chitosan/chitooligosaccharides alone and in combination with chemical fungicides against fungal pathogens", PhD thesis number 2013:12, Norwegian University of Life Sciences (2013) 127 pages.
Tikhonov et al., "Bactericidal and antifungal activities of a low molecular weight chitosan and its N-/2(3)-(dodec-2-enyl)succinoyl/-derivatives", Carbohydrate Polymers, 64:66-72 (2006).

\* cited by examiner

COMPOSITION COMPRISING CHITOSAN AND A FUNGICIDE

The present invention relates to a composition for treating, preventing or controlling fungal disease, damage or infection in plants. Specifically the invention relates to a composition comprising chitosan or chitopoly- or chitooligo-saccharides thereof and a second fungicide not containing chitopoly- or chitooligo-saccharides, and to methods for treating, preventing or controlling fungal disease, damage or infection in plants using said composition. Preferably the chitosan-derived chitopoly- or chitooligo-saccharides of the invention have an average degree of polymerization ($DP_n$) of 10 to 50, preferably 20-40.

Fungi are eukaryotic organisms that lack chlorophyll and thus do not have the ability to photosynthesize their own food. They obtain nutrients by absorption through tiny thread-like filaments called hyphae that branch in all directions throughout a substrate. A collection of hyphae is referred to as mycelium (pl., mycelia). The hyphae are filled with protoplasm containing nuclei and other organelles. Conidiophores are asexual reproductive structures that develop at the tip of hyphae and produces conidia. Mycelia and conidiophores are the key diagnostic signs associated with diseases caused by fungi and fungal-like organisms (FLOs).

Fungal diseases of plants can cause severe pre- and post-harvest losses in agricultural crops. Fungi and FLOs including oomycetes cause the great majority of infectious plant diseases and over 8,000 species have been shown to cause disease. Diseases caused by fungi include all white and true rusts, smuts, needle casts, leaf curls, mildew, sooty moulds and anthracnoses; most leaf, fruit and flower spots; cankers; blights; scabs; root, stem, fruit and wood rots; wilts; and leaf, shoot and bud galls. All economically important plants are thought to be susceptible to attack by one or more fungi and often many different fungi may cause disease in one plant species.

Fungal infections cause pre-harvest damage to crops by killing them outright or weakening them so as to decrease yields and render the plants susceptible to other infections. Post-harvest, fungal infection also results in significant loss of agricultural products during storage, processing and handling. Clearly, there is a significant need to control the fungal infection of plants and plant products and a number of chemical agents have been developed for this purpose, but to date no fully satisfactory agents, i.e. agents that completely control the fungus while at the same time being devoid of undesirable side effects, have been found.

Use of chemical fungicides is the primary method to prevent fungal diseases in plants. Excessive use of synthetic fungicides, however, may cause development of fungicide resistance in the pest population, resulting in the need for higher quantities of the pesticide for effective control. Fungicide residues have been found, for example, in groundwater, animal feed and food for human consumption as a result of pesticide use and can be harmful to animals, including humans. Fungicides may also eliminate beneficial microorganisms which again may result in emergence of "new" diseases. Alternative ways to control plant pathogens are therefore needed so that reduced amounts of chemical fungicides are used while maintaining the same protection against pre- and post-harvest loss caused by fungi and FLOs.

Chitin and chitin-derived molecules such as polymeric and oligomeric chitosan are known to possess antifungal properties. Chitin is a linear polysaccharide consisting of β(1→4) linked N-acetyl-D-glucosamine residues and occurs mainly as a structural component in the cell walls of fungi and yeasts and in the exoskeletons of insects and arthropods (e.g., crabs, lobsters and shrimps). Chitosan can be prepared from chitin by partial deacetylation and is a heteropolymer of N-acetyl-D-glucosamine and D-glucosamine residues. Unlike chitin, chitosan is soluble in water or in dilute aqueous acid solutions. The name chitosan refers to a continuum of soluble polymeric chitin derivatives that can be described and classified according to the fraction of N-acetylated residues ($F_A$) or degree of N-acetylation (DA), the average degree of polymerization ($DP_n$) or the average molecular weight ($M_{Wn}$), the molecular weight distribution (PD, PolyDispersity) and the pattern of N-acetylation ($P_A$) or sequence. Chitosan is non-toxic, biocompatible and biodegradable.

Chitooligosaccharides (CHOS) which encompass chitopoly- or chitooligo-saccharides are oligomers prepared from chitosan either chemically or enzymatically. Chitosan can be converted to CHOS by acid hydrolysis or by enzymatic hydrolysis with glycosyl hydrolases like chitinases or chitosanases. The $F_A$, $M_W$, PD, $DP_n$ and $P_A$ of the resulting CHOS-mixture depend on the chitosan starting material and the specificity of the enzyme used, as well as on reaction conditions such as reaction time, reaction temperature and reaction pH.

Low molecular weight CHOS have been found to be effective against *Candida krusei* and to inhibit spore germination in *Fusarium oxysporum* (Tikhonov, Carbohydr. Polym. 2006, p 66-72). Without wishing to be bound by theory it is believed that the anti-fungal effect of CHOS is dependent on its interaction with lipids in the plasma membrane, leading to morphological changes and cell surface disruption (Palma-Guerrero et al., Fungal Genet. Biol. 2009, p 585-594; Park et al., J. Microbiol. Biotechnol. 2008, p 1729-1734). The composition of the fungal plasma-membrane seems to be important for the sensitivity against chitosan and a higher content of polyunsaturated fatty acids makes the fungi more sensitive (Palma-Guerrero et al., Mol. Microbiol. 2010, p 1021-1032).

Antifungal effects of low molecular weight chitin or chitosan have been published (Kendra & Hadwiger, Experimental Mycology, 1984, p 276-281; Ghaouth et al., Mycol. Res. 1992, p 769-779; U.S. Pat. No. 5,965,545; U.S. Pat. No. 5,374,627; Japanese Patent Application 62-198604; U.S. patent application Ser. No. 08/453,651 and International Publication No. WO 00/59949). Furthermore, a synergistic combination of essential oils and chitosan to control postharvest diseases is described in US Patent 2003/0113421.

Fungicide combinations have been used in the art. The present inventors have identified that the use of chitosan and its chitopoly- or chitooligo-saccharides are particularly useful in a composition also containing a fungicide not containing chitopoly- or chitooligo-saccharides for use as an anti-fungal agent and that a low dose of that latter fungicide may be used. The compositions were found to have broad efficacy.

In particular, as will be described in detail below, preferred chitopoly- or chitooligo-saccharides from chitosan (also referred to as CHOS or chitooligosaccharides herein) were derived from chitosan by specific enzymatic hydrolysis to obtain a defined average oligomeric size ($DP_n$). The fraction of acetylation ($F_A$) of the CHOS is dependent of the $F_A$ of the chitosan from which it is produced. In work leading to the present invention, the present inventors found that chitosan-derived chitopoly- or chitooligo-saccharides, with a specified chemical composition comprising β(1-4)-linked D-glucosamine and N-acetyl-D-glucosamine, boosted the activity of commercial plant protection fungicides leading to a very significant reduction in the amount of the commercial pesticides needed to control both pre- and post-harvest plant diseases. The synergistic effect observed by the inventors from the combination of the chitosan or its chitopoly- or chitooligo-saccharides described herein and the commercial fungicides was much greater than could be expected based on previously reported combinations involving different pesticides. This finding has allowed the development of a more efficient and robust method for protecting plants against air- and soil-borne pathogenic fungi, while at the same time reducing the use of chemical pesticides.

Accordingly, in a first embodiment, the present invention provides a composition comprising (i) chitosan or chitopoly- or chitooligo-saccharides thereof, wherein said chitosan or chitopoly- or chitooligo-saccharides thereof comprise β-(1-4)-linked D-glucosamine and N-acetyl-D-glucosamine monomers and have a degree of acetylation between 0.05 and 0.20 and an average degree of polymerization ≤250 (molecular weight ≤42,000 Da), and (ii) a fungicide not containing chitopoly- or chitooligo-saccharides.

The components of the composition may be provided separately or together, e.g. in a product or kit. Thus in a further aspect, the present invention provides a kit or product comprising (i) chitosan or chitopoly- or chitooligo-saccharides thereof, wherein said chitosan or chitopoly- or chitooligo-saccharides thereof comprise β-(1-4)-linked D-glucosamine and N-acetyl-D-glucosamine monomers and have a degree of acetylation between 0.01 and 0.40, preferably between 0.05 and 0.20, especially preferably 0.10 to 0.20, e.g. 0.15, and an average degree of polymerization ≤250 (molecular weight ≤42,000 Da), and (ii) a fungicide not containing chitopoly- or chitooligo-saccharides, wherein said components (i) and (ii) are presented separately.

Preferred aspects of the invention, as described below, as they relate to the composition of the invention also apply to the product or kit of the invention.

"Chitosan" as referred to herein is a linear soluble polysaccharide composed of β-(1-4)-linked D-glucosamine (deacetylated unit) and N-acetyl-D-glucosamine (acetylated unit) which can be produced by deacetylation of chitin. Chitosan also encompasses chitosan salts. Chitin is a polymer containing β(1-4)-linked N-acetyl-D-glucosamine residues that are linked in a linear fashion. The deacetylation reaction which produces chitosan is rarely conducted to full completion and therefore the chitosan polymeric chain is generally described as a copolymeric structure comprised of D-glucosamine along with N-acetyl-D-glucosamine residues.

The fine structure of chitosan may be defined by the molar fraction of residual N-acetyl-D-glucosamine groups in chitosan expressed as a degree of N-acetylation (DA) or fraction of acetylation ($F_A$). Alternatively the molar fraction of D-glucosamine residues, deacetylation degree (DD), may be used. The degree of deacetylation can be controlled during the chitosan production process.

In contrast to chitin, the presence of free amine groups along the chitosan chain allows this macromolecule to dissolve in water or in dilute aqueous acidic solvents due to the protonation of these groups, rendering the corresponding chitosan salt in solution.

As described in more detail hereinafter, chitosan and the chitosan-derived chitopoly- or chitooligo-saccharide molecules according to the invention may be described herein in terms of their molecular weight ($M_W$) expressed in Daltons (Da) or kilodaltons (kDa) or average degree of polymerization ($DP_n$). The present invention relates to chitosan with a molecular weight of ≤42,000 Da and an $DP_n$≤250.

The chitosan-derived "chitopoly- or chitooligo-saccharides" refer to cleaved portions of larger chitosan molecules. Generally they have a $DP_n$ less than 60, as described hereinafter and preferably are prepared as described hereinafter. Nevertheless, it will be appreciated that the terms "chitosan" and its "chitopoly- or chitooligo-saccharides" are overlapping in scope as smaller chitosan molecules are also chitopoly- or chitooligo-saccharides from larger chitosan molecules. Thus, their molecular weight and $DP_n$ are the determinative factors in terms of size. The chitopoly- or chitooligo-saccharides are also referred to herein collectively as chitooligosaccharides (CHOS) or chitooligomers, poly- or oligo-saccharides derived from chitosan, or simply poly- or oligo-saccharides. Furthermore, it will be appreciated that structurally and functionally equivalent poly- or oligo-saccharides i.e. comprising deacetylated and acetylated units in the preparations described herein, may be derived from sources other than chitosan (or chitin), or they may be produced synthetically.

"Degree of acetylation" (DA) (i.e. N-acetylation, expressed as a percentage) and "fraction of acetylated residues" ($F_A$, expressed as a value between 0 and 1) are used interchangeably herein and describe the molar fraction of residual N-acetyl-D-glucosamine groups in chitosan or the chitopoly- or chitooligo-saccharides derived from chitosan. Chitin generally has a degree of N-acetylation (DA) of more than 70% (i.e. the number of N-acetyl-D-glucosamine monomers is more than 70% and consequently the number of D-glucosamine monomers is less than 30%) and is insoluble in water and weak acidic solutions. Chitosan on the other hand generally has less than 70% DA (the fraction of N-acetyl-D-glucosamine monomers is less than 70% and consequently the fraction of D-glucosamine monomers is more than 30%) and is soluble in dilute acid. Degree of N-acetylation refers to the fraction of N-acetyl-D-glucosamine sugars in the molecule (i.e. 10% N-acetylation is reflected as 0.10); the other sugars are D-glucosamine units. As referred to herein "monomers", "units" and "residues" are used interchangeably to refer to individual saccharide molecules that are linked to form the polymer.

The "average degree of polymerization" $DP_n$) of a chitosan or chitopoly- or chitooligo-saccharide derived therefrom is defined herein as the average number of D-glucosamine and N-acetyl-D-glucosamine monomeric units in a chitosan or polysaccharide or oligosaccharide molecule derived from chitosan. The $DP_n$ of the chitosan polymer comprised in the composition of the present invention is ≤250. (DP denotes the degree of polymerization of individual molecules or a pure composition with identical molecules, i.e. a non-averaged size).

The $DP_n$ values recited herein represent the $DP_n$ of a chitosan/polysaccharide/oligosaccharide preparation and thus encompass both variability in the range of molecules present in the preparation and furthermore in the detection accuracy. In relation to the latter, variation in determining the $DP_n$ may be ±10, e.g. ±5%. Thus for example, a preparation with a $DP_n$ of 30 may have a $DP_n$ ranging from 28.5 to 31.5 depending on the measurement system used. Preferably the measurement is in accordance with the methods used in the Examples (i.e. by $^1$H-NMR spectroscopy).

As mentioned above, variation in the range of molecules present in the preparation exists and the extent of variation may vary. Thus, depending on the preparation method, the molecules in the preparation may be widely divergent in size or the molecules may be of a similar size (e.g. when a size exclusion separation step is used). Preferably the preparation includes molecules of a similar size, e.g. more than 50%, e.g. more than 70, 80, 90, 95 or 99% of the chitosan or chitosan-derived molecules in the preparation have a size that varies no more than 20% (e.g. less than 15, 10, 5 or 1%) from the average $DP_n$. Thus, for example, in a preparation with a $DP_n$ of 30 more than 50% of the molecules preferably have a size (DP) between 24 and 36 (20% deviation).

A "fungicide" as referred to herein is a pesticide that controls fungal disease resulting from infection by a fungus or fungus-like organisms by specifically inhibiting or killing fungi or fungal spores or their growth or spread. As referred to herein a fungicide is a fungicide not containing chitopoly- or chitooligo-saccharides unless explicitly stated otherwise. The "fungicide not containing chitopoly- or chitooligo-saccharides" comprised in the composition of the present invention contains no chitopoly- or chitooligo-saccharides (preferably no chitopoly- or chitooligo-saccharides containing D-glucosamine or N-acetyl-D-glucosamine residues) such as those from chitins, chitosans, or CHOS, e.g. chitopoly- or chitooligo-saccharides from chitin or chitosan with a $DP_n$ from 5 to 250. Preferably the fungicide is a chemical molecule and is not naturally occurring. Chemicals used to control oomycetes are also referred to as fungicides since oomycetes use the same mechanisms as fungi to infect plants. Fungicides can either be contact, translaminar or systemic fungicides. Contact fungicides are not taken up into the plant tissue and only protect the plant where the spray is deposited; translaminar fungicides redistribute the fungicide from the upper, sprayed leaf surface to the lower, unsprayed surface; systemic fungicides are taken up and redistributed through the xylem vessels to the upper parts of the plant.

A "fungus" as referred to herein is any member of a kingdom of organisms (Fungi) that lack chlorophyll, leaves, true stems and roots, reproduce by spores and live as saprotrophs or parasites. The group includes moulds, mildews, rusts, yeasts and mushrooms.

The term "fungus-like organisms" encompasses myxomycetes (slime moulds) and oomycetes which were formerly classified in the kingdom Fungi. Unlike true fungi, the cell walls of these organisms contain cellulose and lack chitin. Oomycetes are a group of heterotrophic organisms generally known as the water moulds and downy mildews. Although oomycetes have similarities to fungi through convergent evolution, they are not fungi (as previously thought); instead, the oomycetes are part of the kingdom Stramenopiles and are thereby distinct from plants, fungi and animals.

The chitopoly- or chitooligo-saccharides used in accordance with the invention may be prepared by various means. CHOS may be prepared from chitosan by using physical methods such as hydrothermal, microwave, ultrasonication and gamma-rays, but these methods are not amenable to the creation of well-defined CHOS mixtures. Chemical methods using acid, $H_2O_2$ or $NaNO_2$ can also yield CHOS. However, enzymatic production of CHOS allows for production of well-defined CHOS mixtures and are more preferred. Such processes are described in more detail below. Chemoenzymatic synthesis may also be used to produce pure CHOS of defined $DP_n$, $F_A$ and $P_A$.

Chitosan may be isolated from the cell walls of certain fungi (e.g. Mucoraceae), but is generally prepared from chitin by homogeneous or heterogeneous deacetylation. Examples of commercially available chitins are those available from sources such as France Chitin, Hov-Bio, Sigma, Sekagaku Corp, Chitinor amongst others. Methods for chitin de-acetylation are well known in the art and some are described in Aranaz, Current Chemical Biology, 2009, 3, p 203-230. The extent of deacetylation may be affected by factors including concentration of the alkali, previous treatment, particle size and density of chitin.

Enzymatic depolymerization of chitin and chitosan involves chitinases and chitosanases, respectively. These methods are described in detail in Aam et al., Mar. Drugs, 2010, 8, p 1482-1517, whereas the various enzyme families comprised by the terms chitinases and chitosanases are described in Hoell et al., Biotechnology and Genetic Engineering, 2010, 27, p 331-366. Chitinases which may be used include those in the glycoside hydrolase (GH) families 18 (e.g. ChiA, B, C) and 19 (e.g. ChiG). Chitinases are also capable of hydrolyzing chitosan, albeit to different extents. Enzymes with chitosanase activity have been found in GH families 5, 7, 8, 46, 75 and 80.

Chitinases are found in plants, microorganisms and animals. Chitinases have been cloned from various species of microorganisms and may be obtained from commercial sources, i.e. companies such as Sigma. Alternatively chitinases may be produced using standard recombinant techniques for protein expression. The scientific literature contains numerous examples of the cloning, overexpression, purification and subsequent application of all types of chitinases (e.g. Horn et al., FEBS J. 2006, p 491-503 and references therein, as well as Hoell et al., 2010, supra).

Unspecific enzymes such as papain and cellulases may also be used to degrade chitosans. These enzymes may be present in mixtures containing minor fractions of chitinases or chitosanases, as well as containing enzymes that do not act on chitin, chitosan or CHOS.

CHOS produced enzymatically or chemically normally consist of a mixture of oligomers differing in DP, $F_A$ and $P_A$. Several techniques for separation and purification of CHOS may be used such as gel filtration, ultrafiltration and ion exchange and metal affinity chromatography. Conveniently size exclusion chromatography (SEC) may be used and oligomers may be detected using an online refractive index detector and this allows separation of CHOS with similar DP values, independently of $F_A$ and $P_A$ (see for example Sørbotten et al., FEBS J., 2005, 272, p 538-549). Further separation of CHOS can be achieved using cation-exchange chromatography. With this method, CHOS of identical DP can be separated based on the number of deacetylated units.

The percent of deacetylated reducing ends generated by the enzymatic cleavage of chitosan may be controlled by selection of the appropriate enzyme as described in the Examples. Published data show that the selection of the enzyme may also be used to affect the percentage of deacetylated residues at other positions in the cleavage products, i.e. positions that were close to the cleavage point, preferably, the newly generated reducing end, the newly generated non-reducing end and the sugars next to each of these two newly generated ends (Horn et al., FEBS J., 2006, p 491-503; Aam et al., Mar. Drugs, 2010, 8, p 1482-1517).

In order to characterize CHOS in terms of $DP_n$, $F_A$ and $P_A$, several techniques known in the art may be used, primarily nuclear magnetic resonance (NMR) and mass spectrometry.

The $DP_n$ of the chitosan or chitopoly- or chitooligo-saccharides therefrom in compositions of the invention is less than or equal to 250. Preferably the average $DP_n$ is between 10 and 250 (molecular weight between 1,680-42,000 Da), e.g. 10 to 50. More preferably the $DP_n$ of the chitosan polysaccharides and oligosaccharides comprised in the composition of the present invention is between 15 and 60, particularly 20 to 40, especially preferably 20 to 35 (molecular weight between 3,320-5,900 Da) or 15 to 35, 15 to 40, 25 to 35 or 30 to 40. In the alternative the $DP_n$ may be between 150 and 250 (molecular weight between 25,200-42,000 Da), e.g. 180 to 220 or 190 to 210. Further preferably the $DP_n$ of the chitosan polysaccharides and oligosaccharides may by any real number 250, e.g. 9, 9.5, 15, 23, 28, 30, 33.5, 34, 34.6, 37, 40, 41, 48, 49, 50, 58, 62, 75, 78, 96, 126, 163 and 206 (preferably 15, 23, 28, 30, 34, 37, 40, 41, 50, 78 or 206) and optionally a range of ±1, 2 or 3 relative to that number, e.g. 23±2, i.e. 21 to 25. As discussed above, experimental variation may account for up to 5 or 10% variation to the values given above. As discussed previously, in a preferred feature the preparation includes molecules of a similar size, e.g. more than 50%, e.g. more than 70, 80, 90, 95 or 99% of the chitosan or chitosan-derived molecules in the preparation have a size that varies no more than 20% (e.g. less than 15, 10, 5 or 1%) from the $DP_n$.

The degree of acetylation of the chitosan or chitopoly- or chitooligo-saccharides therefrom in compositions of the invention is between 0.05 and 0.40, i.e. from 0.05 to 0.40. Preferably the degree of acetylation is from 0.05 to 0.20, preferably from 0.1 to 0.20, e.g. 0.15.

Enhanced performance is observed when the chitosan or chitopoly- or chitooligo-saccharides therefrom have deacetylated reducing ends. Thus, preferably the chitosan or chitopoly- or chitooligo-saccharides therefrom described herein have a D-glucosamine sugar unit at 50% of the reducing ends of the chitosan or chitopoly- or chitooligo-saccharides therefrom, more preferably ≤85%, ≤90%, or ≤95%. The "reducing end" of a chitooligomer comprises a carbon atom that can be in equilibrium with the open-chain aldehyde or keto form.

As described in the Examples, the methods used produce chitooligosaccharides which show high synergy in terms of fungicidal activity when used with fungicides not containing chitopoly- or chitooligo-saccharides. Thus, preferably the chitosan-derived chitopoly- or chitooligo-saccharides are prepared as described in the Examples. Preferably said method comprises dissolving chitosan in water or a weak acidic solution (optionally followed by adjustment of the pH) and then enzymatic cleavage using an enzyme capable of catalysing degradation of chitosan into chitopoly- or chitooligo-saccharides, preferably an enzyme that cleaves the glycosidic bonds after a deacetylated residue (e.g. using a chitosanase such as a family 46 chitosanase, e.g. ScCsn46A, or another non-processive endo-chitosanase that preferably cleaves the glycosidic bond after the deacetylated residue). Site-directed mutants of such enzymes may also be used, which carry mutations that may affect the type or activity of the chitopoly- or chitooligo-saccharides produced and/or the efficiency of the degradation process. Optionally the resultant chitopoly- or chitooligo-saccharide mix may be further separated based on the size of the molecules, e.g. by size exclusion chromatography. Such methods also form part of the invention.

Fungicides which do not contain chitopoly- or chitooligo-saccharides and which may be comprised in the composition of the present invention are preferably selected from one or more of the following groups of fungicides: aliphatic nitrogen fungicides; amide fungicides; acylamino acid fungicides; anilide fungicides; benzanilide fungicides; furanilide fungicides; sulfonanilide fungicides; benzamide fungicides; furamide fungicides; phenylamide fungicides; phenylsulfamide fungicides; sulfonamide fungicides; valinamide fungicides; antibiotic fungicides; strobilurin fungicides; methoxyacrylate strobilurin fungicides; methoxycarbanilate strobilurin fungicides; methoxyiminoacetamide strobilurin fungicides; methoxyiminoacetate strobilurin fungicides; aromatic fungicides; arsenical fungicides; aryl phenyl ketone fungicides; benzimidazole fungicides; benzimidazole precursor fungicides; benzothiazole fungicides; botanical fungicides; bridged diphenyl fungicides; carbamate fungicides; benzimidazolylcarbamate fungicides; carbanilate fungicides; conazole fungicides; copper fungicides; cyanoacrylate fungicides; carboxamide fungicides; dicarboxamide fungicides; dicarboximide fungicides; dichlorophenyl dicarboximide fungicides; phthalimide fungicides; dinitrophenol fungicides; dithiocarbamate fungicides; cyclic dithiocarbamate fungicides; polymeric dithiocarbamate fungicides; dithiolane fungicides; fumigant fungicides; hydrazide fungicides; imidazole fungicides; inorganic fungicides; mercury fungicides; inorganic mercury fungicides; organomercury fungicides; morpholine fungicides; organophosphorus fungicides; organotin fungicides; oxathiin fungicides; oxazole fungicides; polysulfide fungicides; pyrazole fungicides; pyridine fungicides; pyrimidine fungicides; anilinopyrimidine fungicides; pyrrole fungicides; quinoline fungicides; quinone fungicides; quinoxaline fungicides; thiadiazole fungicides; thiazole fungicides; thiazolidine fungicides; thiocarbamate fungicides; thiophene fungicides; triazine fungicides; triazole fungicides; triazolopyrimidine fungicides; urea fungicides; and zinc fungicides. The fungicide may also be a naphthoquinone fungicide. One set of preferred fungicides (not containing chitopoly- or chitooligo-saccharides) may be selected from the above-described groups which excludes antibiotic fungicides (preferably strobilurin fungicides, especially preferably methoxyiminoacetate strobilurin fungicides) and/or thiazole fungicides (preferably conazole fungicides).

The fungicide comprised in the composition of the present invention is preferably selected from one or more fungicides comprised in the following groups: an anilide fungicide, e.g. benalaxyl, benalaxyl-M, bixafen, boscalid, carboxin, fenhexamid, fluxapyroxad, isotianil, metalaxyl, metalaxyl-M, metsulfovax, ofurace, oxadixyl, oxycarboxin, penflufen, pyracarbolid, sedaxane, thifluzamide, tiadinil and vangard; an anilinopyrimidine fungicide, e.g. cyprodinil, mepanipyrim and pyrimethanil; a pyrrole fungicide, e.g. dimetachlone, fenpiclonil, fludioxonil and fluoroimide; a methoxyacrylate strobilurin fungicide, e.g. azoxystrobin, bifujunzhi, coumoxystrobin, enestroburin, jiaxiangjunzhi (coumethoxystrobin), picoxystrobin and pyraoxystrobin; a carbanilate fungicide, e.g. diethofencarb, triclopyricarb, pyraclostrobin and pyrametostrobin; a pyrazole fungicide, e.g. bixafen, fenpyrazamine, fluxapyroxad, furametpyr, isopyrazam, penflufen, penthiopyrad, pyraclostrobin, pyrametostrobin, pyraoxystrobin, rabenzazole and sedaxane; a pyridine fungicide, e.g. boscalid, buthiobate, pyrisoxazole, dipyrithione, fluazinam, fluopicolide, fluopyram, triclopyricarb, parinol, pyribencarb, pyridinitril, pyrifenox, pyroxychlor and pyroxyfur; and a methoxycarbanilate strobilurin fungicide, e.g. triclopyricarb, pyraclostrobin and pyrametostrobin, and combinations thereof. Also preferred are quinone fungicides, e.g. naphthoquinone fungicides, e.g. dithianon, and combinations thereof with the above described fungicides.

Other preferred fungicides are phenylsulfamide, strobilurin, benzimidazole, phthalimide, dithiocarbamate, morpholine, phenylamide, carboxamide, dicarboxamide and anilinopyrimidine fungicides, and combinations thereof.

Preferably the fungicide comprised in the composition of the present invention is selected from one or more of fenhexamid, cyprodinil, fludioxonil, azoxystrobin, boscalid and pyraclostrobin and combinations thereof. Another preferred fungicide is dithianon, and combinations with the above described preferred specific fungicides. The chemical structure of these fungicides is provided below.

Fenhexamid:

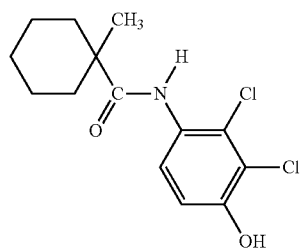 [SMILES: CC1(C(=O)Nc2ccc(O)c(Cl)c2Cl)CCCCC1]

Cyprodinil:

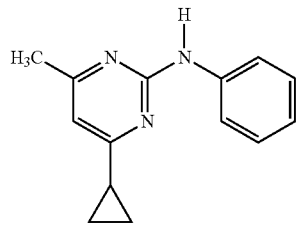 [SMILES: Cc1cc(C2CC2)nc(Nc2ccccc2)n1]

Fludioxonil:

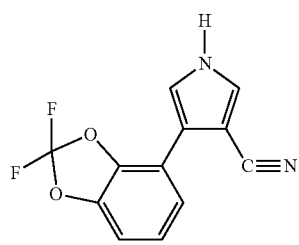 [SMILES: N#Cc1c[nH]cc1-c1cccc2c1OC(F)(F)O2]

Azoxystrobin:

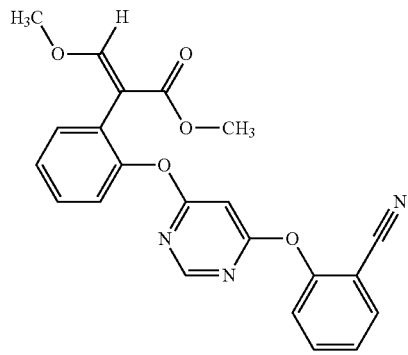 [SMILES: CO/C=C(/C(=O)OC)c1ccccc1Oc1cc(Oc2ccccc2C#N)ncn1]

Boscalid:

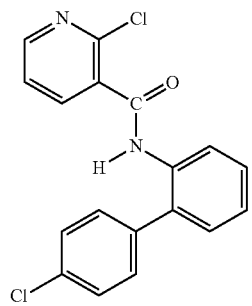 [SMILES: O=C(Nc1ccccc1-c1ccc(Cl)cc1)c1cccnc1Cl]

Pyraclostrobin:

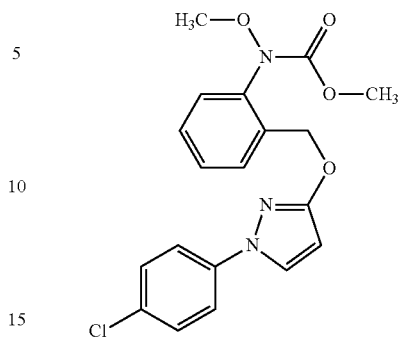

Dithianon:

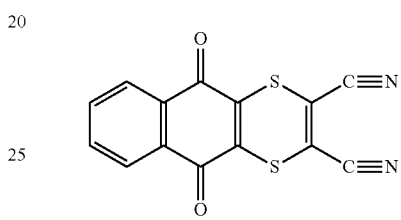

In a preferred embodiment the fungicide comprised in the composition of the present invention is preferably selected from commercially available brands including Teldor® WG 50 (fenhexamid; manufactured by Bayer Crop Science Pty Ltd.), Switch® 62.5 WG (cyprodinil and fludioxonil; manufactured by Syngenta Crop Protection Pty Ltd.), Amistar® (azoxystrobin; manufactured by Syngenta Crop Protection Pty Ltd.), Signum® WG (boscalid and pyraclostrobin; manufactured by BASF) and Stratego® (trifloxystrobin and propiconazole; manufactured by Bayer Crop Science Pty Ltd.). Another preferred fungicide is Delan® WG (dithianon, manufactured by BASF).

Alternative fungicides that may be used include mancozeb and chlorothalonil.

The fungicides described herein are readily available through various commercial sources.

In a further preferred aspect, more than one fungicides may be comprised in the composition together with the chitosan or chitosan-derived molecules. Thus the composition may comprise 1 or alternatively 2, 3, 4 or 5 or more different fungicides which do not contain chitopoly- or chitooligo-saccharides. The preferred aspects of the fungicide as referred to herein apply to all the fungicides (which do not contain chitopoly- or chitooligo-saccharides) which might be present and for the purposes of calculating ratios and optimal concentrations, as described hereinafter, where more than one fungicide which does not contain chitopoly- or chitooligo-saccharides is used it is considered as though it were a single fungicide.

Where more than one fungicide which does not contain chitopoly- or chitooligo-saccharides is present, each fungicide may be present in equal or different proportions relative to one another. Preferably when two fungicides are present they are present in a similar w/w amount, e.g. have a ratio of from 1:1 to 5:1 for the major:minor fungicide. In a preferred example the following combinations of fungicides may be used:

cyprodinil and fludioxonil, preferably at a ratio of 2:1 to 1:1 e.g. 1.5:1; or boscalid and pyraciostrobin, preferably at a ratio of 5:1 to 1:1 e.g. 4:1.

Optionally, other than the one or more fungicides referred to above, no further fungicides which do not contain chitopoly- or chitooligo-saccharides are present in the composition.

The chitosan or chitopoly- or chitooligo-saccharides thereof and the fungicide may be provided in any suitable proportion relative to one another. This is largely dependent on the fungicide to be used and on the pre- or post-harvest plant fungal disease that is being targeted. Thus for example, suitable ratios of chitosan or chitosan-derived material: fungicide ranges from 1000:1 to 1:100 based on a w/w basis in the final composition. Preferably the ratio is greater than 1:1, i.e. from 1000:1 to 1:1. In an alternative preferred aspect similar proportions of the components are provided, e.g. a ratio of 10:1 to 1:10 or 50:1 to 1:2.

As described in the Examples the compositions described herein lead to synergistic fungicidal effects. This allows the dosage of one or both of the components to be reduced, e.g. to a suboptimal concentration relative to the concentration required for fungicidal activity when used alone.

Thus, in a preferred aspect, one or both of the components, preferably the fungicide component (i.e. the component not containing the chitopoly- or chitooligo-saccharides of the present invention) of the composition of the present invention is present in the composition at a suboptimal concentration. A "suboptimal concentration" as referred to herein is any concentration of a fungicide that is lower than the concentration of a particular fungicide which produces the maximum fungicidal effect when used without other fungicidal active ingredients. The optimal working concentration of a fungicide (when used alone) may be lower than the concentration that produces the maximum fungicidal effect for a given fungicide and is often determined and provided by the manufacturer of the fungicide taking other factors into account. Costs as well as regulatory provisions may be taken into account in determining the optimal concentration of a fungicide and thus the recommended optimal concentration may not be the same as that which produces the maximum fungicidal effect, e.g. the optimal concentration may be lower. Consequently, a "suboptimal concentration" of a fungicide as defined herein is lower than the concentration which produces the maximum fungicidal effect (which latter concentration may be the same as the optimal working concentration which is recommended for a particular fungicide or it may be different) when the fungicide is used alone. Preferably the suboptimal concentration is also lower than the optimal working concentration. Thus the optimal working concentration is the concentration used to obtain the best possible fungicidal effect for a fungicide when used alone taking into account all factors influencing the amount of the fungicide that may be used. The concentration of a fungicide achieving the maximum fungicidal effect may be readily determined by the skilled person using one or more methods described in the art, such those described below.

Fungicidal efficacy may be determined by a variety of mechanisms, e.g. as described in the Examples. Thus, for example the inhibition of fungal germination, fungal growth, fungal sporulation, disease severity on the target organism or fungal infection may be used as the determinant of fungicidal activity. Such data may also be obtained from field tests. The result may be expressed as %, $IC_{50}$ and so forth, depending on the test. The concentration at which the optimum fungicidal activity is achieved, taking into account side-effects such as toxicity, may be based on any of these measurements, e.g. disease severity.

Thus a suboptimal concentration of a fungicide (not containing chitopoly- or chitooligo-saccharides) to be comprised in the composition of the present invention may be 90% of the concentration of the fungicide which produces the maximum fungicidal effect (or the optimal concentration of the fungicide) when it is used alone. Alternatively, the concentration of the fungicide may be 80, 70, 60, 50, 40, 30, 20, 19, 18, 17, 16, 15, 14, 13, 12, 11, 10, 9, 8, 7, 6, 5, 4, 3, 2, 1% or less (or less than 1%) of the optimal concentration of the fungicide or the concentration which produces the desired fungicidal effect, e.g. the maximum fungicidal effect. In a preferred embodiment of the invention, the composition comprises 1-20% (or less) of the optimal concentration of the fungicide or the concentration which produces the desired fungicidal effect, e.g. ≤1 (e.g. 0.1 to 1%) or 10% (or less). The above values refer to the amount of the fungicide in its final formulation (e.g. Teldor, Switch etc. as described hereinafter), or the amount of the fungicide alone. When the optimal concentration of a fungicide fails to provide the maximum fungicidal effect, e.g. due to regulatory limitations on the concentration of the fungicide that may be used, the present invention is particularly advantageous as the combination of components of the composition of the invention boosts the activity of the fungicide even at lower concentrations allowing it to reach its maximum fungicidal effect within allowable concentration limits.

The optimal concentration of the fungicide or fungicide mixes used in preferred compositions of the invention are, for example:

Teldor (containing fenhexamid): 1500 µg/ml
Switch (containing cyprodinil+fludioxonil): 500 µg/ml
Amistar (containing azoxystrobin): 1000 µg/ml
Signum (containing boscalid+pyraclostrobin): 1000 µg/ml
Delan (containing dithianon): 800 µg/ml.

Thus sub-optimal concentrations are preferably, respectively, ≤150, 50, 100 and 100 µg/ml respectively (10% of the optimal concentration), or for Delan, ≤80 µg/ml (10% of the optimal concentration), or ≤15, 5, 10 and 10 µg/ml respectively (1% of the optimal concentration), or for Delan, ≤8 µg/ml (1% of the optimal concentration).

The above optimal concentrations may also be expressed by virtue of the constituent fungicide as follows:

Fenhexamid, present at 500 g/kg in Teldor: 750 µg/ml (optimum); 75 µg/ml (10%, sub-optimum); 7.5 µg/ml (1%, sub-optimum), Cyprodinil, present at 375 g/kg in Switch: 187.5 µg/ml (optimum); 18.8 µg/ml (10%, sub-optimum); 1.9 µg/ml (1%, sub-optimum), Fludioxonil present at 250 g/kg in Switch: 125 µg/ml (optimum); 12.5 µg/ml (10%, sub-optimum); 1.3 µg/ml (1%, sub-optimum), Azoxystrobin, present at 500 g/kg in Amistar: 500 µg/ml (optimum); 50 µg/ml (10%, sub-optimum); 5 µg/ml (1%, sub-optimum), Boscalid present at 26.7% in Signum: 267 µg/ml (optimum); 26.7 µg/ml (10%, sub-optimum); 2.7 µg/ml (1%, sub-optimum), Pyraclostrobin present at 6.7% in Signum: 67 µg/ml (optimum); 6.7 µg/ml (10%, sub-optimum); 0.7 µg/ml (1%, sub-optimum), Dithianon present at 70% w/w in Delan: 560 µg/ml (optimum); 56 µg/ml (10%, sub-optimum); 5.6 µg/ml (1%, sub-optimum).

Preferably the fungicidal activity of said chitosan or chitopoly- or chitooligo-saccharides thereof and said fungicide are synergistic, i.e. they have more than additive effects than when used in the same test alone. The presence or absence of synergy can be determined as described in the Examples, and $E_{obs}/E_{exp}$ is >1, preferably >2, >5 or >10.

The composition of the present invention has use in various preventative and therapeutic treatments in plants and thus may be formulated accordingly.

Thus, the composition of the invention may also comprise one or more of the following but not limited to: a stabilizing agent (e.g. by the use of salts or non-electrolytes, acetate, SDS, EDTA, citrate or acetate buffers, mannitol, glycine, HSA or polysorbate), adhesive, anti-foam agent, surface-active agent, chelating agent, dye or colourant and nutrient.

The composition of the invention may be combined with one or more conventional carriers, diluents and/or excipients appropriate for the particular use for the composition, e.g., agriculturally acceptable carriers for agricultural uses, to produce conventional preparations which are suitable or can be made suitable for administration such as powders, sachets, suspensions, emulsions, solutions, aerosols, and the like. They may be formulated as liquids (solutions or suspensions) or as solids.

Examples of suitable carriers, excipients and diluents are lactose, dextrose, sucrose, maltose, glucose, sorbitol, mannitol, starches, gum acacia, calcium phosphate, calcium carbonate, calcium lactose, corn starch, aglinates, tragacanth, gelatin, calcium silicate, polyvinylpyrrolidone, cellulose, water syrup, water, water/ethanol, water/glycol, water/polyethylene, glycol, propylene glycol, methylhydroxybenzoates, propyl hydroxybenzoates, talc, magnesium stearate, mineral oil or fatty substances or suitable mixtures thereof. The compositions may additionally include lubricating agents, wetting agents, emulsifying agents, viscosity increasing agents, granulating agents, disintegrating agents, binding agents, osmotic active agents, suspending agents, preserving agents, adsorption enhancers (e.g. surface penetrating agents, e.g. bile salts, lecithins, surfactants, fatty acids, chelators), organic solvent, antioxidant, stabilizing agents, anti-foaming agent, ionic or non-ionic thickeners, surfactants, filler, ionic or non-ionic thickener, sequestrant, polymer, propellant, alkalinizing or acidifying agent, fatty compounds and the like. The compositions of the invention may be formulated so as to provide quick, sustained or delayed release of the active ingredient after administration to the plant by employing procedures well known in the art.

The use of solutions, suspensions, gels and emulsions are preferred, e.g. the active ingredient may be carried in water, a water-based liquid, an oil, a gel, an emulsion, an oil-in-water or water-in-oil emulsion, a dispersion or a mixture thereof.

The composition of the present invention is preferably water soluble, if necessary by addition of a chemical component(s) such as components to lower the pH, for example organic acids such as acetic acid. The composition may be provided as a wettable (or water soluble) powder or any kind of liquid or mixed with a commercial pesticide as a wettable powder or any kind of liquid. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

The components of the composition may be present as the sole active ingredients or may be combined with other ingredients, particularly other active ingredients, e.g. to augment the fungicidal affect of the composition or the components of the composition.

The compositions can be used as described above for the prevention or treatment of fungal infection in plants.

In a further aspect, the present invention provides a method for treating, preventing or controlling fungal disease, damage or infection in a plant caused by a fungus or fungus-like organism, comprising contacting the plant or part thereof which is affected or to be protected from the fungus with (i) chitosan or chitopoly- or chitooligo-saccharides thereof, wherein said chitosan or chitopoly- or chitooligo-saccharides thereof comprise β-(1-4)-linked D-glucosamine and N-acetyl-D-glucosamine monomers and have a degree of acetylation between 0.01 and 0.40, preferably between 0.05 and 0.20, and an average degree of polymerization ≤250 (molecular weight 42,000 Da), and (ii) a fungicide not containing chitopoly- or chitooligo-saccharides. Components (i) and (ii) are preferably as described hereinbefore.

Alternatively expressed the present invention provides chitosan or chitopoly- or chitooligo-saccharides thereof and a fungicide not containing chitopoly- or chitooligo-saccharides as described hereinbefore for treating, preventing or controlling fungal disease, damage or infection in a plant caused by a fungus or fungus-like organism.

As used herein "treating" refers to the reduction, alleviation or elimination, preferably to normal levels, of one or more of the symptoms of disease, damage or infection, relative to the symptoms or effects present on a different, normal part of the plant or a corresponding normal plant. Such symptoms include levels or extent of fungal germination, fungal growth, fungal sporulation, disease severity (e.g. necrosis or death) on the target organism or level or extent of fungal infection. The severity, level or extent of these symptoms may be determined as described herein. Preferably, where the reduction or alleviation is quantifiable, the symptom(s) is reduced by more than 50%, e.g. >60, 70, 80 or 90%.

"Preventing" refers to absolute prevention, reduction or alleviation of the occurrence of any symptoms of disease, damage or infection, e.g. absence of detectable fungus and fungus-like organism or their parts and/or maintenance of normal levels of detectable fungus and fungus-like organism, or their parts or reduction or alleviation of the extent or timing (e.g. delaying) of the infection with said fungus and fungus-like organism.

Plants treated with the composition described herein preferably have improved or enhanced resistance to fungi and fungal-like organisms in that they show reduced rates of infectivity when compared to non-treated plants. Alternatively, improved resistance to fungi and fungal-like organisms can be apparent in diminished disease symptoms and/or growth, viability, reproduction and dispersal of the pathogen when compared to non-treated plants. The complexity of the mode of action of the components of the composition of the present invention lower the probability of the pathogen developing resistance to the composition, relative to the probability of developing resistance to individual components of the composition.

"Controlling" refers to maintaining the extent of the disease, damage or infection, e.g. reducing or preventing the spread of the infection to other organisms or parts of the plant.

As referred to herein "disease" caused by the fungus or fungus-like organism refers to any adverse effect caused by the fungus or fungus-like organism which affects the function of the plant or part thereof, said function including the quality and commercial value of the possible food or other products derived from the plant "Damage" refers to damage to one or more areas or parts of the plant affected by the fungus or fungus-like organism, e.g. localized necrotic damage.

"Infection" refers to invasion of and multiplication in plant tissues by the fungus or fungus-like organism and is evident from the presence of the fungus or fungus-like organism or its parts (e.g. spores) or damage or disease resulting from its presence.

Preferably, the fungus to be treated, prevented or controlled in plants is a fungal species from genera including *Fusarium, Gliocladium, Rhizoctonia, Trichoderma, Mycosphaerella, Phytophthora, Plasmopora, Leptosphaeria, Cercospora, Rhizoctonia, Cochliobolus, Pseudocercosporella, Pyricularia, Pseudoperonospora, Alternaria* (e.g. *Alternaria brassicicola*), *Pytium, Colletotrichum, Mucor* (e.g. *Mucor piriformis*), *Microdochium* (e.g. *Microdochium majus*), *Uncinula, Ustilago, Erysiphe, Botrytis* (e.g. *Botrytis cineria*), *Saccharomyces, Sclerotium, Candida, Aspergillus* and *Alternaria*. A further preferred fungus is from the genus *Venturia*. Preferably the fungus is *Botrytis cineria, Alternaria brassicicola, Mucor piriformis* or *Microdochium majus*. Another preferred fungus is *Venturia inaequalis*.

Preferably the method is carried out on plants that may be infected or at risk of being infected by plant pathogenic fungi or fungal-like organisms.

The plant to be treated is preferably a cereal (e.g. maize, rice, triticale, *sorghum*, millet, wheat, oats, barley, rye or spelt), a pseudocereal (e.g. buckwheat or quinoa), forage grass, turf grass, grape, root or tuber crop plant (such as potato and carrots), or fruit (e.g. pome fruit), berry, vegetable or pulse crop plant (such as soybeans, peas, chickpeas). Preferred examples include strawberry, chickpea and bean plants. Further preferred examples are pomaceous fruit e.g. apple trees (e.g. *Malus domestica*), stone fruit and vines.

As referred to herein a "part" of a plant refers to seeds, roots, stems, leaves, flowers and fruits or a portion of that part.

The "contacting" step requires that the active ingredient is brought into contact with the plant for an appropriate period of time. Conveniently the two components may be used together and may be used as a single composition (a composition as described herein) or applied simultaneously. In the alternative the two components may be applied sequentially.

Conveniently the components of the composition of the present invention can be applied to all or part of a plant, e.g. the seeds, roots, stems, leaves, flowers and fruits. Alternatively or additionally the treatment can be applied to the soil in which said plant is growing or is to be grown or to the fungus (or fungus-like organism) itself. Normally, application is topical. However, any other administration strategies known to the skilled person can be used.

The components of the composition of the present invention may be applied to the plant or plant part by spraying, dipping or drenching. Alternatively or additionally, they may be applied directly to the fungus or fungus-like organisms by these methods.

Effective concentrations of the chitosan or chitosan-derived molecules are in the range of 1-2000 µg/ml, in liquid preparations for treatment of plants, with about 10-1000 µg/ml being preferred, e.g. 50-150 µg/ml, e.g. 100 µg/ml. Effective amounts of the fungicide which does not contain chitopoly- or chitooligo-saccharides, e.g. a commercial pesticide, are in the range of 1-100%, e.g. 1-20%, of the recommended concentration for the plant/pathogen in question, with 10% (or less) being preferred. Lower concentrations such as 51%, e.g. 0.1 to 1% may also be used. Generally the fungicide not containing chitopoly- or chitooligo-saccharides is present at a concentration of 1 to 300 µg/ml, e.g. 1 to 150 µg/ml, preferably 1 to 100 µg/ml. Even lower concentrations may also be used, e.g. ≤1 µg/ml, e.g. 0.1 to 1 µg/ml. These concentrations act as a guide for developing comparable non-liquid preparations. It is understood, however, that the most favourable concentration of the ingredients will vary depending on the pathogen, its host plant, the disease present, and the administration route. It is well within the level of skill of those in the art to find the most favourable concentrations by following adequate testing procedures.

The determination of an effective amount to be used is well within the scope of the practitioner. An "effective amount" is an amount effective to inhibit the infection, germination or growth of a fungus and fungus-like organism, relative to the infection, germination or growth that is seen in the absence of any such treatment.

Preferred chitosan or chitosan-derived products and fungicide combinations are as follows:

the fungicides fenhexamid (Teldor), cyprodinil and fludioxonil (Switch), azoxystrobin (Amistar) and boscalid and pyraclostrobin (Signum) in combination with chitosan or chitopoly- or chitooligo-saccharides of chitosan with a $DP_n$ of 9, 9.5, 15, 23, 28, 30, 33.5, 34, 34.6, 37, 40, 41, 48, 49, 50, 58, 62, 75, 78, 96, 126, 163 or 206, preferably 15, 23, 28, 30, 34, 37, 40, 41, 50, 78 or 206. The $DP_n$ ranges from 15 to 60, particularly 20 to 40, especially preferably 20 to 35 or 150 to 250 are preferred. Also preferred is the use of the fungicide dithianon (Delan) in combination with such chitosan or chitopoly- or chitooligo-saccharides of chitosan.

Preferably these combinations are used to treat or prevent fungi selected from *Botrytis cineria, Alternaria brassicicola, Mucor piriformis* and *Microdochium majus*. They may also be used to treat *Venturia inaequalis*.

In a further preferred combination the $DP_n$ is 190 to 210, e.g. 206 and the fungicide not containing chitopoly- or chitooligo-saccharides is fenhexamid, cyprodinil and fludioxonil, azoxystrobin or boscalid and pyraclostrobin (preferably fenhexamid or azoxystrobin) and preferably the fungus is *Botrytis cineria* on fruit and berries e.g. on strawberries or *Microdochium* spp., e.g. *Microdochium majus*, on cereals and grasses.

In another preferred combination, the $DP_n$ is 20 to 40, e.g. 30 to 40, e.g. 37 and the fungicide not containing chitopoly- or chitooligo-saccharides is fenhexamid, cyprodinil and fludioxonil, azoxystrobin or boscalid and pyraclostrobin (preferably boscalid and pyraclostrobin) and preferably the fungus is *Botrytis cineria*.

In a yet further preferred combination, the $DP_n$ is 15 to 35, e.g. 20 to 35, e.g. 23 and the fungicide not containing chitopoly- or chitooligo-saccharides is fenhexamid, cyprodinil and fludioxonil, azoxystrobin or boscalid and pyraclostrobin and preferably the fungus is *Botrytis cineria*, e.g. on strawberries.

A further preferred combination is provided by a $DP_n$ of 20 to 40, e.g. 25 to 35, e.g. 30 and the fungicide not containing chitopoly- or chitooligo-saccharides is cyprodinil and fludioxonil or boscalid and pyraclostrobin and preferably the fungus is *Botrytis cineria*, e.g. on chickpeas or beans.

A yet further preferred combination is provided by a $DP_n$ of 20 to 40, e.g. 25 to 35, e.g. 30 and the fungicide not containing chitopoly- or chitooligo-saccharides is dithianon and preferably the fungus is *Venturia inaequalis*, e.g. on pomaceous fruits (such as apples), stone fruits or on vines.

The above described $DP_n$ ranges may also be applied to broader aspects of the invention described hereinbefore.

As described above, the components in the compositions described herein for the indications described above may be used separately.

Thus, in a yet further aspect the present invention provides a product comprising (i) chitosan or chitopoly- or chitooligo-saccharides thereof as described herein and (ii) a fungicide not containing chitopoly- or chitooligo-saccharides as described herein as a combined preparation for simultaneous, separate or sequential use in the treatment or prevention of fungal infection in plants as described herein.

Optionally the compositions and products described herein may contain one or more additional active ingredients.

Also provided is the use of chitosan or chitopoly- or chitooligo-saccharides thereof and a fungicide not containing chitopoly- or chitooligo-saccharides as described herein (or a product, composition or kit as described herein) as a fungicide, preferably for treating, preventing or controlling fungal disease, damage or infection in a plant caused by a fungus or fungus-like organism.

The invention will now be described by way of the following Examples in which:

FIG. 1 shows a size exclusion chromatogram of chitopoly- or chitooligo-saccharides (CHOS) with $DP_n$ 30. The material in the DP>12 areas was fractionated into several samples. The $DP_n$ of the fractions was found using $^1$H-NMR and the material was further used in the biological assays.

FIG. 2 shows the effect on germination of *Botrytis cinerea* 101 of CHOS mixtures with a $DP_n$ of 30, produced by hydrolysis of chitosan $DP_n$ 206 ($F_A$ 0.15) with ScCsn46A, (95% deacetylated reducing ends). Subsequently, subfractions were prepared by separating this hydrolysis mixture using a SEC column as described in the Materials and Methods section. The resulting sub-fractions had $DP_n$ values ranging from 34 to 163.

EXAMPLES

Figure 1:
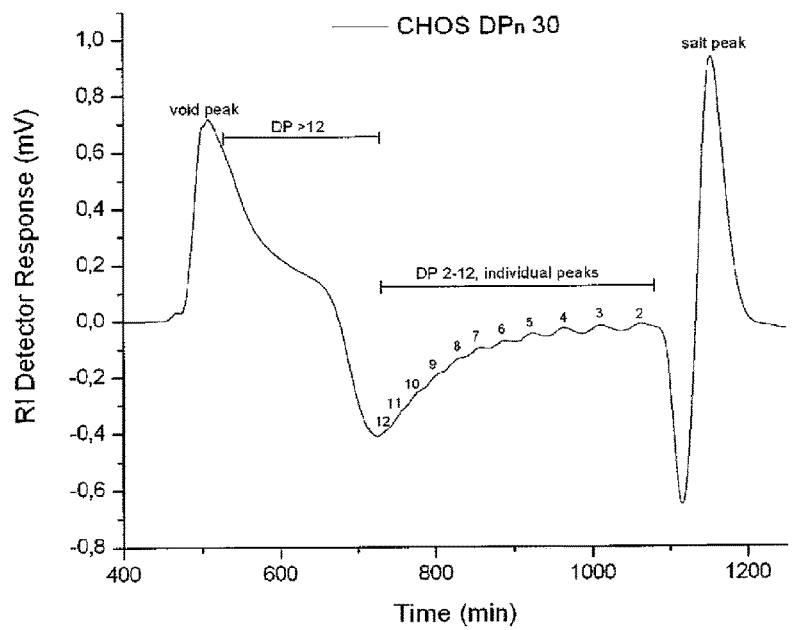

Materials and Methods
Fungal Cultures

*Botrytis cinerea* isolate BC 101, *B. cinerea* BD, *Alternaria brassicicola* A 328, *Microdochium majus* and *Mucor piriformis* M 119 were obtained from the culture collection at the Norwegian University of Life Sciences (UMB). For the in vitro and in vivo bioassays, conidia were collected from cultures grown on potato dextrose agar (FDA) (Difco Laboratories, Detroit, Mich.) under regular laboratory light for 2 weeks at 23±1° C. Concentrations of conidia in aqueous suspensions were determined by haemocytometer count at 400× magnification and adjusted to $4\times10^4$ conidia/ml with sterile water.

Fungicides

Five fungicides not containing chitopoly- or chitooligo-saccharides were used:
1. Teldor@ WG 50 (Bayer Crop Science Pty Ltd.): 500 g/kg fenhexamid. Recommended concentration of Teldor®; 150 g/100 L water
2. Switch® 62.5 WG (Syngenta Crop Protection Pty Ltd.): 375 g/kg cyprodinil, 250 g/kg fludioxonil. Recommended concentration of Switch® 50 g/100 L
3. Amistar® (Syngenta Crop Protection Pty Ltd.): 500 g/kg azoxystrobin. Recommended concentration of Amistar® 100 g/100 L
4. Signum® WG (BASF): 26.7% w/w boscalid and 6.7% w/w pyraclostrobin. Recommended concentration of Signum® 100 g/100 L
5. Delan® WG (BASF): 70% w/w dithianon. Recommended concentration of Delan® 80 g/100 L.

Chitosan and Chitooligosaccharide (CHOS) Production

Chitosan KitoNor ($DP_n$ 206, $F_A$ 0.15, $M_{Wn}$ 34 kDa); was produced by acid hydrolysis from chitin from Snow crab (*Chionoecetes opilio*) by Norwegian Chitosan, Gardermoen, Norway. The average molecular weight and $DP_n$ was calculated from viscosimetric measurements. CHOS with lower $DP_n$ were produced by enzymatic hydrolysis of chitosan ($DP_n$ 206) using a chitosanase, ScCsn46A (Heggset et al., Biomacromolecules, 2010, p 2487-2497), or a chitinase, Chi A (Brurberg et al., FEMS Microbiol Lett., 1994, p 399-404; Horn et al., FEBS J., 2006, p 491-503.).

KitoNor (20 mg/mL) was dissolved in water with 0.5% (v/v) acetic acid. After all of the chitosan was dissolved the pH was adjusted with 0.1N NaOH to 5.5. Recombinant chitosanase ScCsn46A from *Streptomyces coelicolor* A3(2) (Heggset et al., Biomacromolecules, 2010, p 2487-2497) or chitinase A (ChiA) from *Serratia marcescens* (Brurberg et al., FEMS Microbiol Lett., 1994, p 399-404) was added to the chitosan solutions to a final concentration of 0.5 µg/mg chitosan and the reaction was incubated with shaking (225 rpm) at 37° C. The reaction was stopped by decreasing the pH to 2.5 with 0.1N HCl and by keeping the tube with the reaction mixture at boiling temperature for ten minutes to permanently inactivate the enzymes. The $DP_n$ of the resulting CHOS sample was determined by $^1$H-NMR analysis on a Varian 300 mHz instrument, as described in Sørbotten et al. FEBS J., 2005, p 538-549.

Separation of CHOS by Size Exclusion Chromatography (SEC)

The CHOS were separated by SEC on three XK 26 columns packed with Superdex™ 30 prep grade (GE Healthcare) coupled in series with an overall dimension of 2.6 cm×180 cm. The mobile phase (150 mM NH$_4$Ac pH 4.6) was run at a constant flow of 0.4 mL/min (Sørbotten et al. 2005, FEBS J., p 538-549). The signals were read on a RI detector (Gilson model 133). In each run 100 mg of CHOS was applied (i.e. 5 mL) and fractions were collected. Identification of DP$_n$ of the fractions was performed with $^1$H-NMR. The fractions were not baseline separated.

The fractions were dialyzed with Float-A-Lyzers (MWCO 100-500 Da, SpectrumLabs) to remove salts, sterile filtrated through Filtropur S 0.2 μm sterile filters (Sarstedt, Germany) and lyophilized, prior to use.

In Vitro Bioassay of Chitosan and Fungicides Not Containing Chitopoly- or Chitooligo-Saccharides The antifungal effects of chitosan and CHOS samples and fungicides not containing chitopoly- or chitooligo-saccharides were investigated in a synthetic medium (2.5 mM NH$_4$NO$_3$; 0.28 mM CaCl$_2$.2H$_2$O; 0.16 mM MgSO$_4$.7H$_2$O; 0.002 mM MnSO$_4$.4H$_2$O; 0.002 mM ZnSO$_4$.7H$_2$O; 1 mM KH$_2$PO$_4$; 0.06 mM FeC$_6$H$_5$O$_7$.5H$_2$O and 55.5 mM glucose, pH 5.2-5.3) in a flat-bottom 96-well microtiter plate (Nunc™, Roskilde, Denmark), 200 μL/well with 2×10$^4$ conidia/mL. There were 4 replicate wells of each treatment. The microtiter plates were incubated at 23±1° C. for up to 72 h. An invert microscope (Fluovert FU, Ernst Leitz Wetzlar GmbH, Wetzlar, Germany) was used to visually estimate the germination percentage at 400× magnification after 24 h and these estimates were used to express antimicrobial activity as half maximal inhibitory concentrations (IC$_{50}$) or minimum inhibitory concentrations (MIC). Mycelial growth following germination was measured as absorbance at 595 nm in a microtiter plate reader 72 h after inoculation.

Synergistic effects were calculated as the ratio between observed efficacy, E$_{obs}$ (% inhibition) and the expected efficacy, E$_{exp}$ (calculated by Abbott's formula) (Levy et al. Eppo Bulletin, 1986, p 651-657) % E$_{exp}$=−(ab/100). Here a=% germination inhibition by that concentration of the fungicide alone, b=% germination inhibition by that concentration of the chitosan alone. An E$_{obs}$/E$_{exp}$ ratio of 1 indicates additivity, ratios >1 indicates synergy and ratios <1 indicates antagonistic interactions.

In Vivo Bioassay of Chitosan and Fungicides Not Containing Chitopoly- or Chitooligo-Saccharides on Plants The flower infection test was performed on detached, newly opened strawberry (*Fragaria*×*ananassa*) flowers (cv. Corona) from the greenhouse (Hjeljord et al. Phytopathology, 2001, p 1172-1180). Eighteen flowers per treatment (six replications of three flowers) were cut off with a 1½-2 cm stem and placed in empty pipette tip racks set in plastic containers filled with 1-2 cm water. Conidia suspensions of the pathogen (final concentration: 1×10$^6$ conidia/ml) were mixed with test ingredients (i.e. fungicides, CHOS, chitosan or mixtures thereof, as well as control ingredients) and 10 μl drops of each mixture were placed at the base of three petals on each flower using an automatic pipette (Finnpipette 4027, Thermo Labsystems, Finland). All flowers were then incubated at 23±1° C. in large trays covered with aluminium foil. The relative humidity around the flowers was 90-95%, measured by a thermo-hygrometer (Lambrecht, Germany).

The necrotic regions on the abaxial surface of the flowers under the inoculation point were recorded daily for 8 days and the area under the disease progress curve (AUDPC) was calculated on the basis of the cumulative infection percentage by the following equation:

$$\text{AUDPC} = \Sigma[(D_i - D_{i-1}) \times \{S_i - 1 + 0.5(S_i - S_{i-1})\}]$$

Where, D$_i$=Days of the i$^{th}$ assessment, S$_i$=Proportion of the i$^{th}$ infected inoculation point.

The protection index was calculated by using the AUDPC values in the following equation (Bardin et al., Biological Control, 2008, p 476-483).

$$100 \times (\text{AUDPC}_{control} - \text{AUDPC}_{treatment})/\text{AUDPC}_{control}$$

where AUDPC$_{control}$ represents flowers inoculated with only *B. cinerea* conidia and AUDPC$_{treatment}$ represents flowers treated with the conidia applied in solutions containing pesticides and/or chitooligosaccharides to be tested. The interaction (synergy) between fungicides and the chitosan products in the flower assay was determined by Abbott's equation as above.

Similar tests were performed on detached chickpea leaves (*Cicer arientinum*) (3×6 leaves per treatment and 3 parallels), or on 30 day-old bean leaves (*Vicia faba*) (6 inoculation drops on each leaf and 3 parallels). The leaves were inoculated with 10 μL drops with 2×10$^6$/ml *B. cinerea* 101 conidia. The development of the disease and the amount of sporulation were recorded every 24 hours up to 8 days. The experiment was repeated at least twice.

Field Trials with Chitosan and the Fungicides Not Containing Chitopoly- or Chitooligo-Saccharides Apple trees (*Malus domestica* Broch) of the cultivar Aakerø in the apple orchard at the Norwegian University of Life Sciences, Aas, Norway were used. There were three replicates of each treatment and three trees in each replicate. The trees were sprayed to runoff once in the flowering period (28$^{Th}$ of May) and three times in the fruiting season (24$^{th}$ of June, 7$^{th}$ of July and 17$^{th}$ of August). At harvest (3$^{rd}$ of September) the number of apples with infection of apple scab (*Venturia inaequalis*) was recorded.

Determination of Average Degree of Polymerization (DP$_n$) with $^1$H-NMR Spectroscopy The chitooligosaccharide (CHOS) samples were analysed by $^1$H-NMR spectroscopy on a Varian Gemini 300 MHz instrument. The average degree of polymerization (DP$_n$) was calculated by the equation (Dα+Dβ+D+Aα+Aβ+A)/(Dα+Dβ+Aα+Aβ), where Dα, Dβ, Aα and Aβ are the integral of the reducing end signals of the α and β anomers of the deacetylated (D) and acetylated (A) units, D is the integral of the signals from the internal and nonreducing end deacetylated units and A is the integral of the signals from the internal and nonreducing end acetylated units (Sørbotten et al. FEBS J., 2005, p 538-549).

Data Analysis

The % inhibition data for the fungal germination were transformed using arcsine transformation and tested by one-way ANOVA (analysis of variance). Non-transformed data are presented. When appropriate, means were separated by Tukey's method (Fenech, J Am. Stat. Ass., 1979, p 881-884). All calculations were done using Microsoft Office Excel 2007 and Minitab 16 (MINITAB, USA).

Example 1: Production of Chitooligosaccharides (CHOS)

Chitosan KitoNor (DP$_n$ 206, F$_A$ 0.15 and M$_W$ 34 kDa) was hydrolyzed with chitosanase ScCsn46A, which primarily cleaves after deacetylated units and under the conditions of the assay produced 95% deacetylated reducing ends, as determined by $^1$H-NMR). The chitooligomers were separated by SEC (see Materials and Methods) and the results are shown in FIG. 1. These chitooligosaccharides of varying $DP_n$ were used in Example 2. For details see Materials and Methods: "Chitosan and chitooligosaccharide (CHOS) production".

Example 2: Effect of $DP_n$ of CHOS on Fungicidal Activity (Inhibition of Germination)

The effect of chitosan ($F_A$ 0.15, $DP_n$ 206), or chitooligosaccharides (CHOS), obtained by hydrolysis of this chitosan with ScCsn46A to $DP_n$ values varying from 9.5 to 96 (95% deacetylated reducing ends, as determined by $^1$H-NMR) on spore germination of Botrytis cinerea 101 was evaluated. The experiment was conducted as described in the Materials and Methods section under "In vitro bioassay".

The $DP_n$ of the chitosan/CHOS influences the inhibitory effect on the germination of B. cinerea 101. The most active fractions have $DP_n$ values in the order of 30, but the data also show that $DP_n$ values in the range of 10-40 have useful activities (Table 1).

TABLE 1

Effect of $DP_n$ of CHOS on fungicidal activity (inhibition of germination)

| $DP_n$ of chitosan/CHOS | MIC (µg $ml^{-1}$) | $IC_{50}$ (µg $ml^{-1}$) |
|---|---|---|
| 206 | 5000 | 2500 |
| 96 | 2500 | 1230 |
| 62 | 2500 | 630 |
| 49 | 2500 | 630 |
| 40 | 1200 | 250 |
| 37 | 310 | 80 |
| 28 | 310 | 80 |
| 15 | 310 | 120 |
| 9.5 | >2500 | 2500 |

$IC_{50}$ = half maximal inhibitory concentrations.
MIC = minimum inhibitory concentrations.

Example 3: Effect of Deacetylated Reducing Ends in CHOS on Fungicidal Activity (Inhibition of Germination)

An in vitro assay of the fungicidal activity of chitosan and CHOS with >95% (chitosan hydrolysed by chitosanase ScCsn46A from Streptomyces coelicolor) or 35% (chitosan hydrolysed by chitinase A from Serratia marcescens) deacetylated reducing ends was carried out as described in the Materials and Methods section under "In vitro bioassay". The results are shown in FIG. 3.

Figure 3:
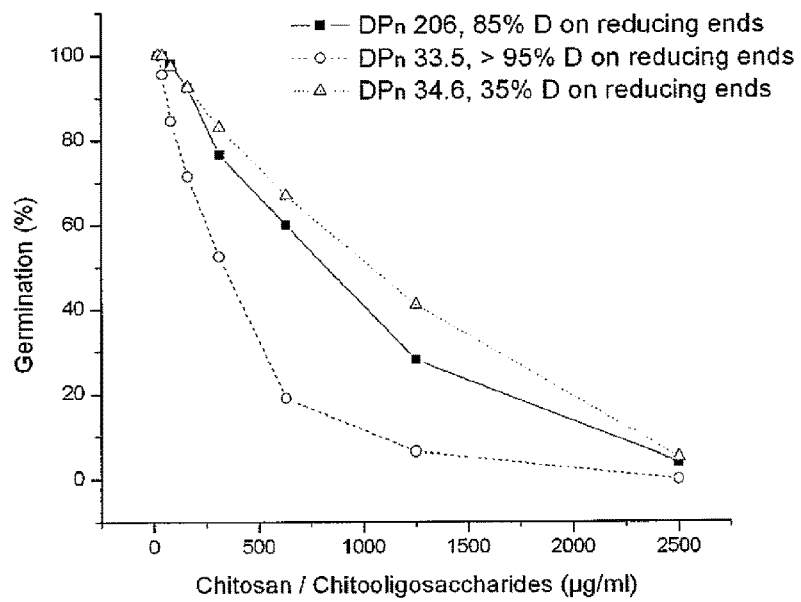
FIG. 3 shows the effect of acetylation of reducing end sugars on the ability of CHOS to inhibit germination of *B. cinerea* 101. CHOS with 95% deacetylated reducing ends was obtained by hydrolyzing chitosan ($F_A$ 0.15, $DP_n$=206) with ScCsn46A, whereas CHOS with 35% deacetylated reducing ends was obtained by hydrolyzing the same chitosan with ChiA.

Given the same $DP_n$, CHOS with deacetylated reducing ends are much more inhibitory to spore germination than CHOS with acetylated reducing ends (FIG. 3). For example, 80 µg $ml^{-1}$ CHOS with 95% deacetylated reducing ends prevented further hyphal growth, whereas 310 µg $ml^{-1}$ CHOS with 35% deacetylated reducing ends was needed to attain the same effect (data not shown).

Example 4: Effect of Partial Purification of CHOS with Various $DP_n$ on Fungicidal Activity (Inhibition of Germination)

Figure 2:
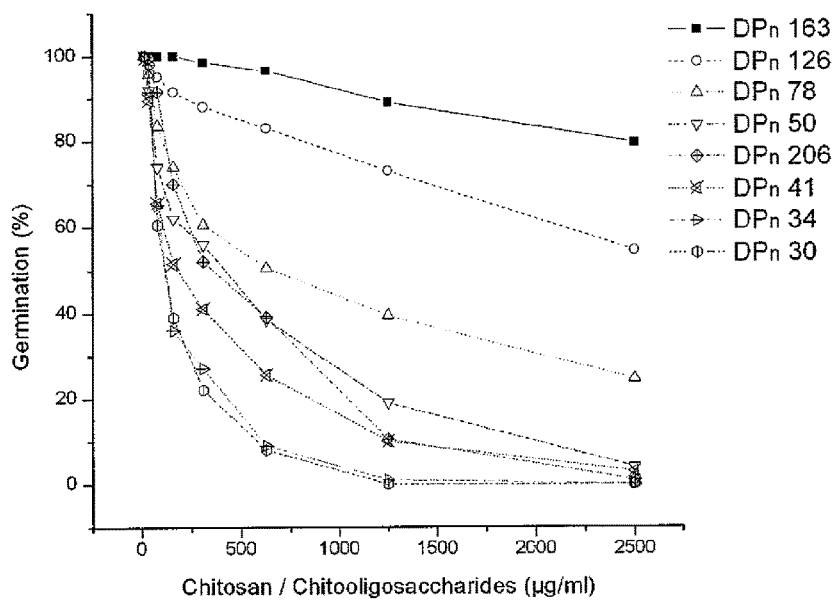

This experiment assessed the effect of partially purified chitooligosaccharides (CHOS) with varying chain lengths on the germination inhibition of B. cinerea 101, assessed 24 hours after inoculation. Purification was by SEC, see the Materials and Methods section. The results are shown in FIG. 2 and demonstrate that sub-fractions with high $DP_n$ ($DP_n$ 78-163) are less inhibitory than the original non-hydrolyzed chitosan $DP_n$ 206, probably due to the removal of low molecular weight oligomers from those fractions. The CHOS $DP_n$ 30 hydrolysate that had not been separated further on the SEC column had about the same inhibitory effect as the $DP_n$ 34 SEC fraction. The non-purified $DP_n$ 30 and the purified $DP_n$ 34 fractions were the most inhibitory of the fractions tested.

Example 5: Effect of Chitosan or CHOS with Various $DP_n$ on Germination or Growth of Different Fungi An experiment was designed to assess effects of chitosan and CHOS with various $DP_n$ on germination and mycelial growth of two strains of B. cinerea and a strain of Mucor piriformis. This experiment assessed germination inhibition (GI) and growth inhibition (Gr.I) of B. cinerea 101 (BC 101), B. cinerea BD (BC BD) and Mucor piriformis M 119 caused by 80 µg $ml^{-1}$ non-hydrolyzed chitosan and chitooligosaccharides (CHOS) ($F_A$ 0.15) with different $DP_n$, produced by enzymatic hydrolysis with ScCsn46A (95% deacetylated reducing ends). Growth inhibition was measured by absorbance reading at 595 nm 72 hours after inoculation.

The results, depicted in Table 2, show that CHOS with average $DP_n$ between 23 and 40 were generally more inhibitory to spore germination and growth than CHOS with higher or lower average $DP_n$. The data further show that the inhibitory effect of the compounds varies depending on the target organism.

TABLE 2

Effect of chitosan or CHOS with various $DP_n$ on germination inhibition (GI %) or growth inhibition (Gr.I %) of different fungi
Chitosan/CHOS

| | BC 101 | | BC BD | | M. piriformis | |
|---|---|---|---|---|---|---|
| $DP_n$ | GI % 24 hrs | Gr.I % 72 hrs | GI % 24 hrs | Gr.I % 72 hrs | GI % 24 hrs | Gr.I % 72 hrs |
| 206 | 0 c | 14 e | 0 c | 7 e | 0 g | 23 c |
| 75 ± 6.8 | 4 c | 36 d | 0 c | 25 d | 26 e | 48 b |
| 58 ± 2.7 | 0 c | 50 cd | 0 c | 42 c | 50 d | 53 ab |
| 48 ± 3.0 | 4 c | 54 c | 0 c | 46 c | 48 d | 51 ab |
| 40 ± 1.4 | 77 a | 99 a | 100 a | 99 a | 90 a | 57 a |
| 23 ± 1.3 | 72 b | 76 b | 100 a | 78 b | 81 b | 57 a |
| 15 ± 1.4 | 0 c | ND | 100 a | ND | 58 c | ND |
| 9 ± 0.8 | 0 c | 6 e | 0 c | 3 e | 0 g | 22 c |

Means in columns without common letters are significantly different according to Tukey's method at P ≤ 0.01.
ND = not determined.

Example 6: Effect of Chitosan or CHOS with Various $DP_n$ on Disease Severity Caused by Two Strains of B. cinerea A bioassay was designed to assess effects of non-hydrolyzed chitosan and CHOS with various $DP_n$ on infection of strawberry flowers by two strains of B. cinerea. In this experiment the effect on the disease severity caused by B. cinerea 101 and B. cinerea BD on detached strawberry flowers treated with 500 µg/mL chitosan or chitooligosaccharides (CHOS) ($F_A$ 0.15 and 95% deacetylated reducing ends) with different $DP_n$ was assessed. The CHOS fractions with lower $DP_n$ were produced by enzymatic hydrolysis of chitosan ($DP_n$ 206) using a chitosanase, ScCsn46A. For details see Materials and Methods section: "Chitosan and chitooligosaccharide (CHOS) production". The disease severity was assessed as area under the disease progress curve (AUDPC), calculated from cumulative disease incidence at 23±1° C., 1 to 8 days after inoculation.

The results in Table 3 show that CHOS with $DP_n$ 23 are more protective against *B. cinerea* infection of strawberry flowers than CHOS with higher and lower $DP_n$. Of the other products tested, the $DP_n$ 40 material clearly shows the best results.

TABLE 3

Effect of chitosan or CHOS with various $DP_n$ on disease severity caused by two strains of *B. cinerea* on strawberry flowers

| Chitosan/CHOS | *B. cinerea* 101 | | *B. cinerea* BD | |
|---|---|---|---|---|
| | AUDPC | Protection index (%) | AUDPC | Protection index (%) |
| Control | 4.3 a | — | 4.3 a | — |
| $DP_n$ 206 | 4.0 ab | 7.8 c | 3.5 a | 19.8 d |
| $DP_n$ 48 | 3.4 b | 20.3 c | 2.8 c | 34.5 c |
| $DP_n$ 40 | 1.9 c | 55.2 b | 1.7 d | 61.5 b |
| $DP_n$ 23 | 0.9 d | 79.8 a | 0.7 e | 83.6 a |
| $DP_n$ 9 | 4.0 ab | 7.0 c | 3.5 a | 19.0 d |

Means in columns without common letters are significantly different according to Tukey's method at P ≤ 0.01.

Example 7: Effect of CHOS with $DP_n$ 37 on Germination of Different Fungi

Figure 4:
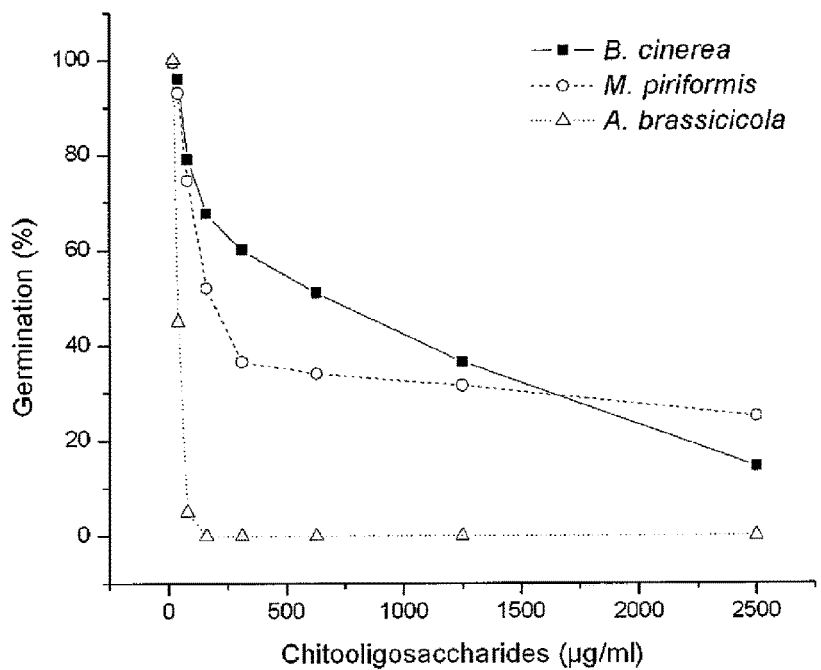
FIG. 4 shows the results of an experiment to assess dose-response relationships of CHOS $DP_n$ 37 (prepared by hydrolyzing with ScCsn46A) on germination of *B. cinerea* 101, *Alternaria brassicicola* A 328 and *Mucor piriformis* M 119.

An experiment was designed to compare effects of CHOS ($DP_n$ 37) on three genera of plant pathogenic fungi. As seen in FIG. 4, the results show a dose-response relationship for all genera tested, but these did respond somewhat differently. *B. cinerea* and *M. piriformis* showed decreasing germination over a broad CHOS concentration range (0.002-0.25%), whereas *A. brassicicola* showed complete germination at 0.002% and none at 0.008%.

Example 8: Fungicidal Activity of Chitosan and the Fungicide Switch (Inhibition of Germination) on Two Strains of *B. cinerea*

Non-hydrolyzed chitosan was mixed with a fungicide (Switch) to compare the effects of the mixture and the components separately on germination of two strains of *B. cinerea*. This experiment evaluated germination inhibition of *B. cinerea* 101 or *B. cinerea* BD recorded 24 hours after inoculation with chitosan ($DP_n$ 206) and/or the fungicide Switch.

The results are provided in Table 4 and show that Switch applied at 25 μg ml$^{-1}$, a concentration that is only 1/20 of the recommended concentration (the recommended concentration, 500 μg ml$^{-1}$, are according to the standard product leaflets provided by the manufacturers of this product) together with 640 μg/ml chitosan $DP_n$ 206 completely inhibited spore germination of both *Botrytis* strains. The combinations were clearly synergistic.

TABLE 4

Fungicidal activity of chitosan and the fungicide Switch (inhibition of germination) on two strains of *B. cinerea*

| Treatment | % inhibition of *B. cinerea* 101 | % inhibition of *B. cinerea* BD |
|---|---|---|
| Chitosan 640 μg ml$^{-1}$ | 32 d | 17 d |
| Chitosan 80 μg ml$^{-1}$ | 11 c | 5 e |
| Switch 25 μgml$^{-1}$ | 82 b | 43 c |
| Chitosan 640 μg ml$^{-1}$ + Switch 25 μg ml$^{-1}$ | 100 a | 100 a |
| Chitosan 80 μg ml$^{-1}$ + Switch 25 μg ml$^{-1}$ | 100 a | 90 b |

Means in columns without common letters and related to the same fungicide, are significantly different according to Tukey's method at P ≤ 0.01.

Example 9: Fungicidal Activity of Chitosan and the Fungicides Switch or Signum (Inhibition of Germination) on *Microdochium majus*

Further experiments assessed the effects of combining chitosan with fungicides (Switch or Signum) on germination of the plant pathogenic fungus *Microdochium majus*. This experiment evaluated germination inhibition of *M. majus* recorded 24 h after inoculation with chitosan ($DP_n$ 206) and fungicides. For details see Materials and Methods: "In vitro bioassay of chitosan and fungicides not containing chitopoly- or chitooligo-saccharides".

The results in Table 5 show that combination of 640 μg ml$^{-1}$ chitosan $DP_n$ 206 with Switch at 1/50 of recommended concentration (recommended concentration is 500 μg ml$^{-1}$) or Signum at 1/1000 of recommended concentration (recommended concentration is 1000 μg ml$^{-1}$), completely inhibited spore germination of *M. majus*. Recommended concentrations of Switch and Signum are according to the standard product leaflets provided by the manufacturers of these products.

TABLE 5

Fungicidal activity of chitosan and the fungicides Switch or Signum (inhibition of germination) on *Microdochium majus*

| Treatment | % inhibition of *M. majus* |
|---|---|
| Chitosan 640 μg ml$^{-1}$ | 3 d |
| Switch 10 μg ml$^{-1}$ | 71 b |
| Signum 1 μg ml$^{-1}$ | 26 c |
| Chitosan 640 μg ml$^{-1}$ + Switch 10 μg ml$^{-1}$ | 100 a |
| Chitosan 640 μg ml$^{-1}$ + Signum 1 μg ml$^{-1}$ | 100 a |

Means in columns without common letters and related to the same fungicide, are significantly different according to Tukey's method at P ≤ 0.01.

Example 10: Fungicidal Activity of CHOS with $DP_n$ 23 and the Fungicides Teldor, Switch, Amistar and Signum (Inhibition of Germination) on *B. cinerea*

Possible synergism between CHOS ($DP_n$ 23) and fungicides (Teldor, Switch, Amistar and Signum) in inhibition of germination of *B. cinerea* was investigated in this experiment. The effect of combination of chitooligosaccharides (CHOS) $DP_n$ 23 ($F_A$ 0.15 and 95% deacetylated reducing ends) and fungicides in inhibiting germination (assessed 24 hours after inoculation) of *B. cinerea* BC 101 was assessed.

The results are shown in Table 6 which shows that high synergistic effects are seen when combining 5 μg $DP_n$ 23 with 1% of the recommended concentration of Switch, Amistar and Signum and 10% of the recommended concentration of Teldor. Comparison of the data in Table 6 with the data in Table 4 further shows that the $DP_n$ 23 product is more powerful than the non-hydrolyzed chitosan with $DP_n$ 206.

TABLE 6

Fungicidal activity of CHOS with $DP_n$ 23 and the fungicides Teldor, Switch, Amistar and Signum (inhibition of germination) on B. cinerea 101

| Treatment (μg/ml) | Germination inhibition (%) | $E_{obs}/E_{exp}$ |
|---|---|---|
| Control | 0 b | — |
| $DP_n$ 23 5 μg ml$^{-1}$ | 1 b | — |
| Teldor 150 μg ml$^{-1}$ | 0 b | — |
| $DP_n$ 23 5 μg ml$^{-1}$ + Teldor 150 μg ml$^{-1}$ | 20 a | 20 |
| $DP_n$ 23 5 μg ml$^{-1}$ | 1 c | — |
| Switch 5 μg ml$^{-1}$ | 30 b | — |
| $DP_n$ 23 5 μg ml$^{-1}$ + Switch 5 μg ml$^{-1}$ | 94 a | 3 |
| $DP_n$ 23 5 μg ml$^{-1}$ | 1 b | — |
| Amistar 10 μg ml$^{-1}$ | 2 b | — |
| $DP_n$ 23 5 μg ml$^{-1}$ + Amistar 10 μg ml$^{-1}$ | 92 a | 31 |
| $DP_n$ 23 5 μg ml$^{-1}$ | 1 b | — |
| Signum 10 μg ml$^{-1}$ | 1 b | — |
| $DP_n$ 23 5 μg ml$^{-1}$ + Signum 10 μg ml$^{-1}$ | 98 a | 49 |

Means in columns without common letters and related to the same fungicide, are significantly different according to Tukey's method at P ≤ 0.01. Synergism is calculated by the $E_{obs}/E_{exp}$ ratio, 1 indicates additivity, ratios >1 indicate synergy and ratios <1 indicate antagonistic interactions. The recommended concentrations for application of Teldor, Switch, Amistar and Signum are 1500, 500, 1000, 1000 μg/ml, respectively, according to the standard product leaflets provided by the manufacturers of these products.

Example 11: Fungicidal Activity of Chitosan and the Fungicides Teldor, Switch, Amistar and Signum (Inhibition of Infection of Strawberry Flowers) on B. cinerea A bioassay was designed to evaluate effects of the combination of chitosan and fungicides (Teldor, Switch, Amistar or Signum) on flower infection by B. cinerea 101. For experimental details see: In vivo bioassay of chitosan and fungicides on plants, infection on strawberry flowers in Materials and Methods section. This experiment assessed the effect of combination of chitosan with $DP_n$ 206 and fungicides in μg ml$^{-1}$ in inhibiting B. cinerea BC 101 infection of detached strawberry flowers. Disease severity was measured as the area under the disease progress curves (AUDPC), with AUDPC values calculated from the cumulative disease incidence at 23±1° C., recorded up to 8 days after inoculation. Percent protection index is % reduction in AUDPC by the treatment compared with the control.

The results are shown in Table 7 which shows that 1% of the recommended concentration of Teldor, Switch and Amistar (15, 5 and 10 μg/ml respectively) in combination with 1000 μg chitosan $DP_n$ 206 and 5000 μg ml$^{-1}$ chitosan in combination with 0.2% of the recommended concentration of Signum (2 μg/ml), gave the same level of protection against infection by B. cinerea as the recommended concentration of the respective fungicides alone.

TABLE 7

Fungicidal activity of chitosan and the fungicides Teldor, Switch, Amistar and Signum (inhibition of infection of strawberry flowers) on B. cinerea

| Treatment (all concentrations in μg ml$^{-1}$) | AUDPC | Protection index (%) | $E_{obs}/E_{exp}$ |
|---|---|---|---|
| Untreated control | 4.8 a | — | — |
| Chitosan 5000 | 2.5 de | 49 cd | — |
| Chitosan 1000 | 2.9 cd | 39 de | — |
| Chitosan 400 | 3.7 bc | 24 ef | — |

TABLE 7-continued

Fungicidal activity of chitosan and the fungicides Teldor, Switch, Amistar and Signum (inhibition of infection of strawberry flowers) on B. cinerea

| Treatment (all concentrations in μg ml$^{-1}$) | AUDPC | Protection index (%) | $E_{obs}/E_{exp}$ |
|---|---|---|---|
| Teldor 1500 | 1.5 fg | 69 ab | — |
| Teldor 15 | 4.4 ab | 9 f | — |
| Chitosan 1000 + Teldor 15 | 1.5 fg | 70 ab | 2 |
| Chitosan 400 + Teldor 15 | 1.9 ef | 61 bc | 2 |
| Switch 500 | 1.0 g | 79 a | — |
| Switch 5 | 4.5 a | 7 f | — |
| Chitosan 1000 + Switch 5 | 1.5 fg | 70 ab | 2 |
| Chitosan 400 + Switch 5 | 1.8 efg | 63 abc | 2 |
| Amistar 1000 | 2.0 ef | 59 bc | — |
| Amistar 10 | 4.5 a | 7 f | — |
| Chitosan 1000 + Amistar 10 | 1.8 efg | 63 abc | 2 |
| Chitosan 400 + Amistar 10 | 1.8 efg | 63 abc | 2 |
| Signum 1000 | 1.3 fg | 72 ab | — |
| Signum 10 | 4.2 ab | 13 f | — |
| Signum 2 | 4.5 a | 7 f | — |
| Chitosan 400 + Signum 10 | 2.1 ef | 56 bc | 2 |
| Chitosan 400 + Signum 2 | 2.5 de | 49 cd | 2 |

Means in columns without common letters and related to the same fungicide, are significantly different according to Tukey's method at P ≤ 0.01. The recommended concentrations for application of Teldor, Switch, Amistar and Signum are 1500, 500, 1000 and 1000 μg/ml respectively, according to the standard product leaflets provided by the manufacturers of these products.

Example 12: Fungicidal Activity of CHOS with $DP_n$23 and the Fungicides Teldor, Switch, Amistar and Signum (Reduction in Disease Severity on Strawberry Flowers) on B. cinerea Possible synergism between CHOS ($DP_n$ 23) and fungicides (Teldor, Switch, Amistar and Signum) in reduction of disease severity in inoculated strawberry flowers was assessed in this experiment. For experimental details see: In vivo bioassay of chitosan and fungicides not containing chitopoly- or chitooligo-saccharides on plants, infection on strawberry flowers in the Materials and Methods section. This experiment assessed the effect of a chitooligosaccharide (CHOS) $DP_n$ 23 ($F_A$ 0.15 and 95% deacetylated reducing ends) alone and in combination with fungicides in inhibiting B. cinerea BC 101 infection of detached strawberry flowers, assessed using the area under the disease progress curve (AUDPC), to calculate the protection index and synergy. Disease severity was measured as the area under disease progress curve (AUDPC), with AUDPC values calculated from the cumulative disease incidence at 23±1° C., recorded up to 8 days after inoculation.

The results in Table 8 shows that 10 μg ml$^{-1}$ of CHOS $DP_n$ 23 in combination with 10% of the recommended dose (150 μg ml$^{-1}$) of Teldor, 5% of the recommended dose (25 μg ml$^{-1}$) of Switch, 1% of the recommended dose (10 μg ml$^{-1}$) of Amistar and 1% of the recommended dose (10 μg ml$^{-1}$) of Signum gave the same or better protection against infection by B. cinerea than the fungicides alone, applied at their recommended concentrations. Comparison of the data in Table 8 with the data in Table 7 further shows that the $DP_n$ 23 product is more powerful than the non-hydrolyzed chitosan with $DP_n$ 206. For example 10 μg/ml $DP_n$ 23+10 μg/ml Signum gave better protection than 400 μg/ml $DP_n$ 206+10 μg/ml Signum.

TABLE 8

Fungicidal activity of CHOS with $DP_n$ 23 and the fungicides Teldor, Switch, Amistar and Signum (reduction in disease severity on strawberry flowers) on B. cinerea

| Treatment (µg ml⁻¹) | AUDPC | Protection Index (%) | $E_{obs}/E_{exp}$ |
|---|---|---|---|
| Untreated control | 4.6 a | — | |
| $DP_n$ 23 10 µg ml⁻¹ | 4.5 a | 2 f | |
| Teldor 1500 µg ml⁻¹ | 1.5 | 68 cd | |
| Teldor 150 µg ml⁻¹ | 2.3 b | 51 e | |
| Switch 500 µg ml⁻¹ | 1.0 | 78 | |
| Switch 25 µg ml⁻¹ | 4.2 a | 9 f | |
| Amistar 1000 µg ml⁻¹ | 2.0 | 57 de | |
| Amistar 10 µg ml⁻¹ | 4.5 a | 2 f | |
| Signum 1000 µg ml⁻¹ | 1.3 d | 71 bc | |
| Signum 10 µg ml⁻¹ | 4.5 a | 1 f | |
| $DP_n$ 23 10 µg ml⁻¹ + Teldor 150 µg ml⁻¹ | 0.5 e | 89 a | 2 |
| $DP_n$ 23 10 µg ml⁻¹ + Switch 25 µg ml⁻¹ | 0.7 e | 84 a | 8 |
| $DP_n$ 23 10 µg ml⁻¹ + Amistar 10 µg ml⁻¹ | 0.8 e | 82 ab | 21 |
| $DP_n$ 23 10 µg ml⁻¹ + Signum 10 µg ml⁻¹ | 0.6 e | 87 a | 30 |

Percent protection index is % reduction in AUDPC by the treatment compared with the control. Synergism is calculated by the $E_{obs}/E_{exp}$ ratio, 1 indicates additivity, ratios >1 indicates synergy and ratios <1 indicates antagonistic interactions. Means in columns without common letters and related to the same fungicide, are significantly different according to Tukey's method at P ≤ 0.01. The recommended concentrations for application of Teldor, Switch, Amistar and Signum are 1500, 500, 1000 and 1000 µg ml⁻¹ respectively, according to the standard product leaflets provided by the manufacturers of these products.

Example 13: Fungicidal Activity of Chitosan or CHOS with $DP_n$ 30 and the Fungicide Switch (Reduction of Infection on Chickpea Leaves) on B. cinerea Possible synergism between non-hydrolyzed chitosan, CHOS ($DP_n$ 30) and Switch in reducing infection of chickpea leaves by B. cinerea 101 was investigated. For experimental details see: In vivo bioassay of chitosan and fungicides not containing chitopoly- or chitooligo-saccharides on plants, infection on chickpea leaves in the Materials and Methods section.

Figure 5:
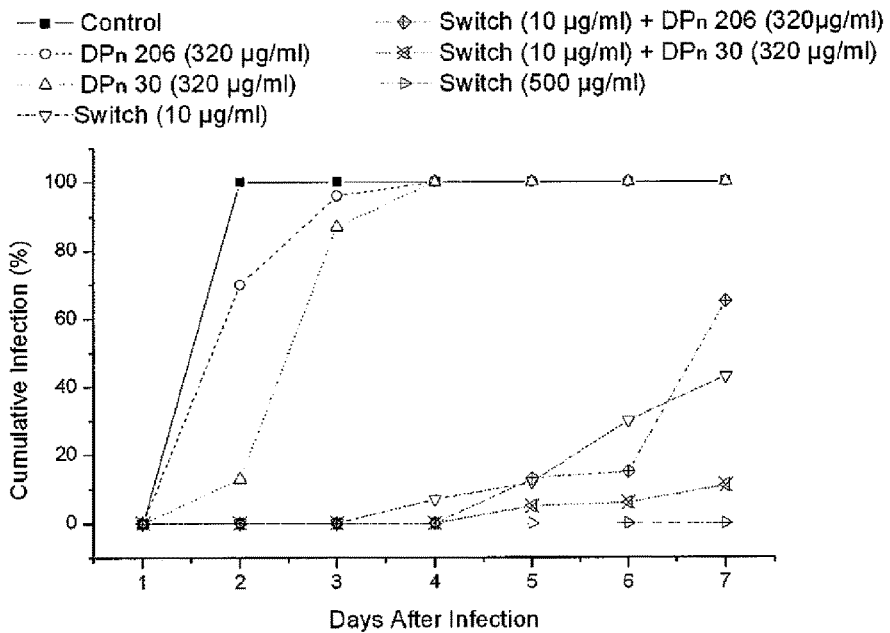
FIG. 5 shows the results of an experiment to assess the effect of combinations of chitosan $DP_n$ 206, CHOS $DP_n$ 30 ($F_A$ 0.15 and 95% deacetylated reducing ends) and Switch on the cumulative infection of detached chickpea leaves by *B. cinerea* 101.

The results, depicted in FIG. 5, show that, when combined with Switch, CHOS ($DP_n$ 30) was much more effective than the non-hydrolyzed chitosan ($DP_n$ 206). The figure also illustrates the power of CHOS: the combination of ¹/₅₀ of the recommended Switch concentration (10 µg ml⁻¹) (recommended concentration is 500 µg ml⁻¹) with 320 µg ml⁻¹ CHOS ($DP_n$ 30) was as protective as the recommended concentration of Switch.

Example 14: Fungicidal activity of chitosan or CHOS with $DP_n$ 30 and the fungicide Signum (reduction of infection on chickpea leaves) on B. cinerea 101

This experiment was similar to that described in Example 13, except that the fungicide Signum was tested. For experimental details see: In vivo bioassay of chitosan and fungicides not containing chitopoly- or chitooligo-saccharides on plants, infection on chickpea leaves in the Materials and Methods section.

Figure 6:
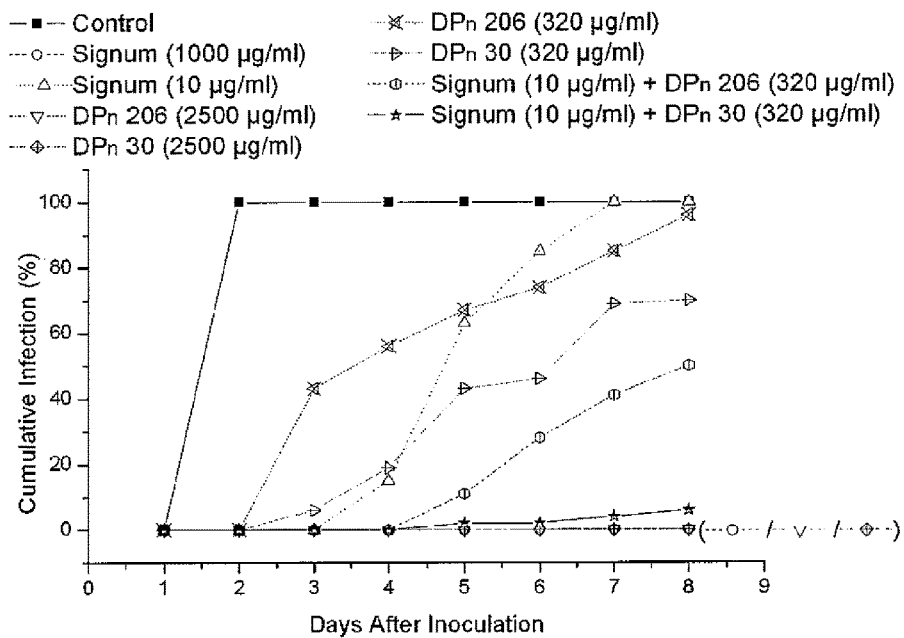
FIG. 6 shows the results of an experiment to assess the effect of the combination of chitosan $DP_n$ 206, CHOS $DP_n$ 30 ($F_A$ 0.15 and 95% deacetylated reducing ends) and Signum (Sig) on infection of detached chickpea leaves by *B. cinerea* 101.

The results are shown in FIG. 6. FIG. 6 shows that all combinations of chitosan $DP_n$ 206 and the CHOS $DP_n$ 30 with Signum showed a better effect in reducing disease severity than each component alone. 1000 µg ml⁻¹ Signum, 2500 µg ml⁻¹ chitosan $DP_n$ 206 and 2500 µg ml⁻¹ $DP_n$ 30 completely controlled infection, whereas the combination of 10 µg ml⁻¹ Signum and 320 µg ml⁻¹ CHOS $DP_n$ 30 resulted in only 5% infection after 8 days. These results illustrate the synergistic effect of CHOS with a reduced concentration of Signum.

Example 15: Fungicidal Activity of Chitosan or CHOS with $DP_n$ 30 and the Fungicide Signum (Reduction of Sporulation on Infected Chickpea Leaves) on B. cinerea 101

Sporulation of the plant pathogenic fungus on infected plant parts is a source of secondary inoculum and an important factor in disease epidemiology. An experiment was designed to assess the effects of the combination of chitosan or CHOS with the fungicide Signum on sporulation of B. cinerea on infected chickpea leaves. This experiment assessed the effect of combination of chitosan $DP_n$ 206, or chitooligosaccharide (CHOS) $DP_n$ 30 and Signum on the average number of spores produced after 8 days by B. cinerea 101 in each inoculation spot on chickpea leaves. For experimental details see: In vivo bioassay of chitosan and fungicides on plants not containing chitopoly- or chitooligo-saccharides, infection on chickpea leaves in the Materials and Methods section.

The results in Table 9 show that the combination of chitosan and Signum reduced sporulation of B. cinerea 101 more than each component alone and CHOS $DP_n$ 30 was more effective than chitosan $DP_n$ 206 when each were combined with Signum in reducing the sporulation of B. cinerea 101.

TABLE 9

Fungicidal activity of chitosan or CHOS with $DP_n$ 30 and the fungicide Signum (reduction of sporulation on infected chickpea leaves) on B. cinerea 101

| Treatment | Average number of conidia produced in inoculation point |
|---|---|
| Untreated control | $2.1 \times 10^5$ |
| Signum 10 µg ml⁻¹ | $3.6 \times 10^4$ |
| Chitosan $DP_n$ 206, 320 µg ml⁻¹ | $7.8 \times 10^4$ |
| CHOS $DP_n$ 30, 320 µg ml⁻¹ | $4.1 \times 10^4$ |
| Signum 10 µg ml⁻¹ + Chitosan $DP_n$ 206, 320 µg ml⁻¹ | $7.8 \times 10^3$ |
| Signum 10 µg ml⁻¹ + CHOS $DP_n$ 30, 320 µg ml⁻¹ | $2.9 \times 10^2$ |

Example 16: Fungicidal Activity of Chitosan or CHOS with $DP_n$ 30 and the Fungicide Switch (Reduction of Infection on Bean Leaves) on B. cinerea An experiment was designed to assess the effects of the combination of chitosan or CHOS with the fungicide Switch on B. cinerea 101 infection of bean leaves. For experimental details see: In vivo bioassay of chitosan and fungicides not containing chitopoly- or chitooligo-saccharides on plants, infection on bean leaves in the Materials and Methods section.

Figure 7:
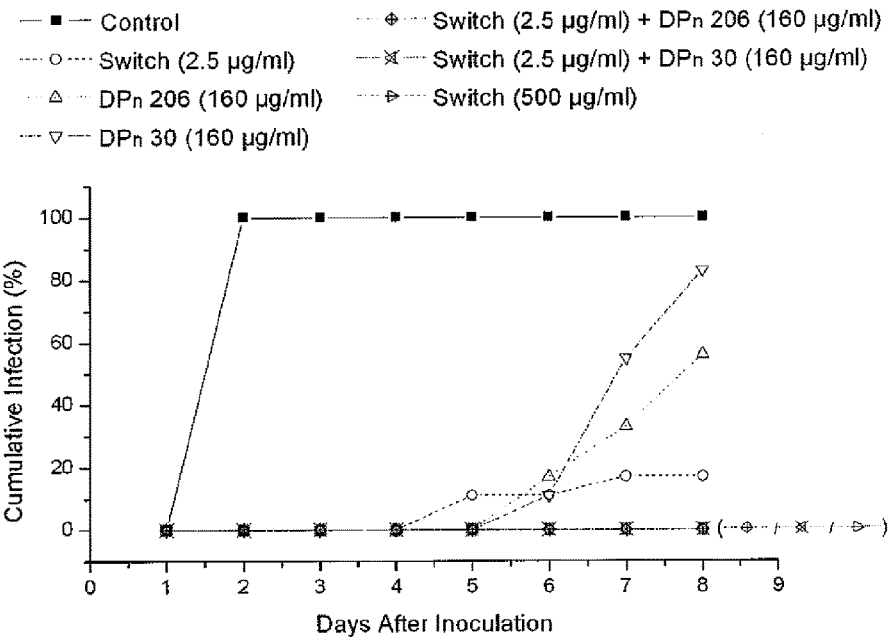
FIG. 7 shows the results of an experiment to assess the effect of the combination of chitosan $DP_n$ 206, CHOS $DP_n$ 30 and Switch on *B. cinerea* 101 infection of bean leaves.

The results are shown in FIG. 7. In this assay 500 µg ml⁻¹ Switch (recommended concentration) and the combination of 2.5 µg ml⁻¹ Switch and 160 µg ml⁻¹ of $DP_n$ 30 or $DP_n$ 206 chitosan completely controlled infection, while 2.5 µg ml⁻¹ Switch, or 160 µg ml⁻¹ chitosan $DP_n$ 206 or CHOS $DP_n$ 30 separately were less effective.

Example 17: Fungicidal Activity of Chitosan or CHOS with $DP_n$ 30 and the Fungicide Signum (Reduction of Infection on Bean Leaves) on *B. cinerea* 101

This experiment was similar to that described in Example 16, except that the fungicide Signum was tested. For experimental details see: In vivo bioassay of chitosan and fungicides not containing chitopoly- or chitooligo-saccharides on plants, infection on bean leaves in the Materials and Methods section.

Figure 8:
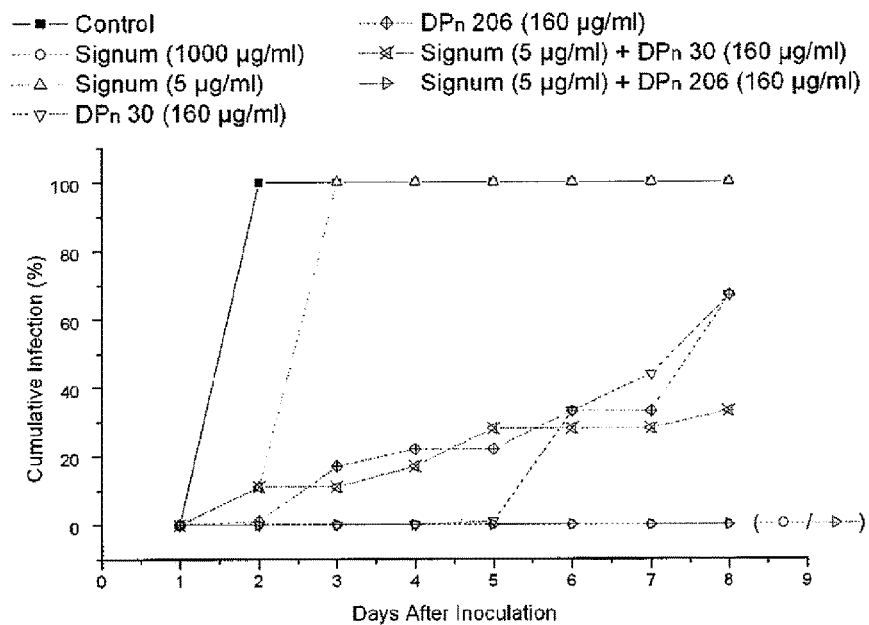
FIG. 8 shows the results of an experiment to assess the effect of chitosan $DP_n$ 206, the CHOS $DP_n$ 30 and Signum (Sig) on *B. cinerea* 101 infections of bean leaves.

The results are shown in FIG. 8 which shows that in this assay, complete control of infection was obtained by 1000 µg ml$^{-1}$ Signum (recommended concentration), or the combination of 5 µg ml$^{-1}$ Signum+160 µg ml$^{-1}$ chitosan $DP_n$ 206.

Example 18: Field Experiment for Testing the Fungicidal Activity of CHOS with $DP_n$ 30 and the Fungicide Delan Against Apple Scab (*Venturia inaequalis*)

In a field trial the effect of 0.1% CHOS and recommended (0.8%) and 1/10 concentration (0.08%) of Delan on the infection of *Venturia inaequalis* on apples was investigated. For experimental details see: Field trials with chitosan and the fungicides not containing chitopoly- or chitooligo-saccharides in the Materials and Methods section.

The results in Table 10 shows that the combination of CHOS and 1/10 of the recommended concentration of Delan was more effective than the recommended concentration of Delan

TABLE 10

Fungicidal activity of CHOS with $DP_n$ 30 and the fungicide Delan (reduction of apples with apple scab) on *Venturia inaequalis*.

| Treatment | % apple with apple scab |
|---|---|
| Untreated control | 31.2 ± 9.7$^a$ |
| Delan 0.8 g/L (800 µg ml$^{-1}$) | 20.9 ± 9.5 |
| Delan 0.08 g/L (80 µg ml$^{-1}$) | 27.5 ± 12.0 |
| CHOS $DP_n$ 30, 1.0 g/L (1000 µg ml$^{-1}$) | 25.9 ± 13.3 |
| Delan 80 µg ml$^{-1}$ + Chitosan $DP_n$ 30, 1000 µg ml$^{-1}$ | 16.7 ± 5.2 |

$^a$Standard deviation

The invention claimed is:

1. A composition comprising
 (i) chitooligo-saccharides, wherein said chitooligo-saccharides comprise β-(1-4)-linked D-glucosamine and N-acetyl-D-glucosamine monomers and have a degree of acetylation between 0.01 and 0.40 and an average degree of polymerization of 20-60 as assessed by measurement with $^1$H NMR spectroscopy, and
 (ii) a fungicide not containing chitopoly- or chitooligo-saccharides;
 wherein said fungicide is not an inorganic fungicide;
 wherein the fungicidal activity of said chitooligo-saccharides and said fungicide is synergistic;
 wherein the chitooligo-saccharides are present in the composition at a concentration of 1-1000 µg/ml;
 wherein the chitooligo-saccharides and said fungicide are present in a ratio of 1000:1 to 1:2 (w/v); and
 wherein the fungicide is selected from the group consisting of an anilide fungicide; an anilinopyrimidine fungicide; a pyrrole fungicide; a methoxyacrylate strobilurin fungicide; a carbanilate fungicide; a pyrazole fungicide; a pyridine fungicide; a methoxycarbanilate strobilurin fungicide, a naphthoquinone fungicide, a benzamide fungicide, a strobilurin fungicide, a conazole fungicide, a carboxamide fungicide, a triazole fungicide, and a dicarboximide fungicide, and combinations thereof.

2. The composition as claimed in claim 1 having an average degree of polymerization ($DP_n$) of between 20 to 40.

3. The composition as claimed in claim 1 wherein the $DP_n$ is 23, 30, or 40.

4. The composition as claimed in claim 1 wherein ≥50% of the polymer chains in the chitooligo-saccharides have a D-glucosamine sugar unit at their reducing ends.

5. The composition as claimed in claim 1 where said chitooligo-saccharides are prepared by acid hydrolysis.

6. The composition as claimed in claim 1 where said chitooligo-saccharides are prepared by a method comprising dissolving chitosan in water or a weak acidic solution followed by enzymatic cleavage using an enzyme capable of catalysing degradation of chitosan into chitooligo-saccharides.

7. The composition as claimed in claim 5 wherein the resultant chitooligo-saccharide product mix is separated by size exclusion chromatography.

8. The composition as claimed in claim 1 wherein the chitooligo-saccharides are present in the composition at a concentration between 10 and 1000 µg/ml.

9. The composition as claimed in claim 1 wherein the fungicide is selected from the group consisting of fenhexamid, cyprodinil, fludioxonil, azoxystrobin, boscalid, pyraclostrobin and dithianon, and combinations thereof.

10. The composition as claimed in claim 1 wherein at least 2 fungicides not containing chitopoly- or chitooligo-saccharides are present.

11. The composition as claimed in claim 1 wherein the fungicide is present in the composition at a suboptimal concentration.

12. The composition as claimed in claim 11 wherein the concentration of the fungicide in the composition is 1-20% of the optimal concentration of the fungicide.

13. The composition as claimed in claim 1 wherein the fungicide is selected from (i) fenhexamid; (ii) cyprodinil and fludioxonil; (iii) azoxystrobin; (iv) boscalid and pyraclostrobin and (v) dithianon and the chitooligo-saccharides have a $DP_n$ of between 20 and 60.

14. A kit comprising (i) chitooligo-saccharides and (ii) a fungicide, wherein each component is as defined in claim 1.

15. A method for treating fungal disease, damage or infection in a plant caused by a fungus, comprising contacting the plant or part thereof which is affected by the fungus with an effective amount of the composition of claim 1.

16. The method as claimed in claim 15 wherein the method is carried out on plants and the fungus is selected from *Botrytis cineria, Alternaria brassicicola, Mucor piriformis, Microdochium* sp and *Venturia inaequalis*.

17. The method as claimed in claim 15 wherein the plant is a cereal, turf grass, rice, grape or root, tuber, fruit, berry, vegetable or pulse crop plant.

18. A method for treating fungal disease, damage or infection in a plant caused by a fungus comprising contacting the plant or part thereof which is affected by the fungus with an effective amount of the composition of claim 13.

19. The composition of claim 1 wherein said chitooligo-saccharides have a degree of acetylation between 0.05 and 0.20.

20. The composition of claim 2 having an average degree of polymerization ($DP_n$) of between 20 to 35.

21. The composition of claim 12 wherein the concentration of the fungicide in the composition is <10% of the optimal concentration.

22. The composition of claim 13 wherein the chitooligosaccharides have a $DP_n$ of 20 to 40.

23. The composition of claim 13 wherein the chitooligosaccharides have a $DP_n$ of 20 to 35.

24. The composition of claim 13 wherein the chitooligosaccharides have a $DP_n$ of 23, 30, or 37.

* * * * *